United States Patent
McCoy et al.

(10) Patent No.: US 10,610,101 B2
(45) Date of Patent: Apr. 7, 2020

(54) ARM FATIGUE ANALYSIS SYSTEM

(71) Applicants: Gary McCoy, Gilbert, AZ (US);
Timothy W. Markison, Mesa, AZ (US)

(72) Inventors: Gary McCoy, Gilbert, AZ (US);
Timothy W. Markison, Mesa, AZ (US)

(73) Assignee: ATHALONZ, LLC, Mesa, AZ (US)

( * ) Notice: Subject to any disclaimer, the term of this patent is extended or adjusted under 35 U.S.C. 154(b) by 426 days.

(21) Appl. No.: 14/812,868

(22) Filed: Jul. 29, 2015

(65) Prior Publication Data
US 2017/0028256 A1    Feb. 2, 2017

(51) Int. Cl.
*A61B 5/00*    (2006.01)
*G06K 9/00*    (2006.01)
*A61B 5/11*    (2006.01)
*G16H 50/30*    (2018.01)
*G16H 20/30*    (2018.01)

(52) U.S. Cl.
CPC .............. *A61B 5/002* (2013.01); *A61B 5/11* (2013.01); *A61B 5/1114* (2013.01); *G06K 9/00342* (2013.01); *G16H 20/30* (2018.01); *G16H 50/30* (2018.01)

(58) Field of Classification Search
CPC ............ A63B 24/0003; A63B 2220/62; A63B 2220/20; G16H 50/30; G16H 20/30; G06K 9/00; A61B 5/00; A61B 5/11
See application file for complete search history.

(56) References Cited

U.S. PATENT DOCUMENTS

| | | | | |
|---|---|---|---|---|
| 4,303,241 A * | 12/1981 | Burroughs | ............. | A61F 9/029 273/DIG. 17 |
| 6,571,193 B1 * | 5/2003 | Unuma | ................ | A43B 3/0005 340/853.2 |
| 7,264,554 B2 * | 9/2007 | Bentley | ................ | A61B 5/1122 382/107 |
| 7,891,666 B2 * | 2/2011 | Kuenzler | ............... | A63B 43/00 273/108 |
| 8,308,615 B2 * | 11/2012 | Vitolo | .................. | A61B 5/1036 482/1 |
| 8,337,335 B2 * | 12/2012 | Dugan | ............... | A63B 69/3623 473/212 |

(Continued)

OTHER PUBLICATIONS

Mark Derewicz, Curveballs, sliders and pitch counts: Surviving life as a pitcher with your arm intact, Endeavors magazine, pp. 1-4.*

(Continued)

*Primary Examiner* — Xuan M Thai
*Assistant Examiner* — Malinda D. Blaise
(74) *Attorney, Agent, or Firm* — Garlik & Markison; Timothy W. Markison

(57) ABSTRACT

A method includes collecting, for a pitch, per pitch data that includes a plurality of first arm orientation data points and a plurality of second arm orientation data points. The method further includes analyzing the per pitch data to determine a release point arm orientation and an effort level. The method further includes calculating a per pitch stress level based on the release point arm orientation and the effort level. The method further includes calculating, for a set of pitches, a fatigue level based on the per pitch stress level of each pitch of the set of pitches.

20 Claims, 18 Drawing Sheets

(56) References Cited

U.S. PATENT DOCUMENTS

| | | | | |
|---|---|---|---|---|
| 8,602,922 B2* | 12/2013 | Schwenger | A63B 49/00 | 473/549 |
| 9,161,708 B2* | 10/2015 | Elliott | A63B 71/06 | |
| 9,195,219 B2* | 11/2015 | Hong | G04G 21/00 | |
| 9,308,417 B2* | 4/2016 | Grundy | A63B 24/0062 | |
| 9,881,326 B2* | 1/2018 | Gilley | G06Q 30/02 | |
| 2002/0077189 A1* | 6/2002 | Tuer | A63B 69/3632 | 473/151 |
| 2005/0017454 A1* | 1/2005 | Endo | G06F 3/016 | 273/317.1 |
| 2006/0025229 A1* | 2/2006 | Mahajan | A63B 24/0003 | 473/131 |
| 2008/0076637 A1* | 3/2008 | Gilley | G06F 19/3475 | 482/9 |
| 2010/0216578 A1* | 8/2010 | Mejia Perez | A63B 69/0002 | 473/452 |
| 2011/0190912 A1* | 8/2011 | Paul | G06F 19/00 | 700/93 |
| 2012/0316843 A1* | 12/2012 | Beno | G06Q 10/0639 | 703/2 |
| 2013/0053190 A1* | 2/2013 | Mettler | G09B 19/0038 | 473/463 |
| 2013/0244211 A1* | 9/2013 | Dowling | G06F 19/3481 | 434/247 |
| 2013/0274040 A1* | 10/2013 | Coza | G09B 19/0038 | 473/570 |
| 2013/0274904 A1* | 10/2013 | Coza | G06F 3/011 | 700/91 |
| 2013/0310958 A1* | 11/2013 | Sanchez | A63B 24/0062 | 700/91 |
| 2014/0277636 A1* | 9/2014 | Thurman | A63B 71/0605 | 700/91 |
| 2014/0278219 A1* | 9/2014 | Canavan | A63B 24/0062 | 702/150 |
| 2015/0019135 A1* | 1/2015 | Kacyvenski | A61B 5/0488 | 702/19 |
| 2015/0196803 A1* | 7/2015 | Shavit | A63B 71/0622 | 482/8 |
| 2015/0260512 A1* | 9/2015 | Greiner | A63B 71/0616 | 702/150 |
| 2016/0232807 A1* | 8/2016 | Ghaffari | G09B 19/00 | |
| 2016/0303455 A1* | 10/2016 | Carswell | A61B 5/0531 | |
| 2017/0061817 A1* | 3/2017 | Mettler May | G09B 19/003 | |
| 2017/0156662 A1* | 6/2017 | Goodall | A61B 5/4836 | |
| 2017/0164876 A1* | 6/2017 | Hyde | A61B 5/1118 | |
| 2017/0319133 A1* | 11/2017 | Coza | A61B 5/6804 | |

OTHER PUBLICATIONS

Atwell, Cabe. "Baseball Players can Avoid Injury with the Motus Smart-Sleeve." Web blog post. Wearable Technology. Element14 Community, Nov. 26, 2014. Web. May 11, 2015.

* cited by examiner

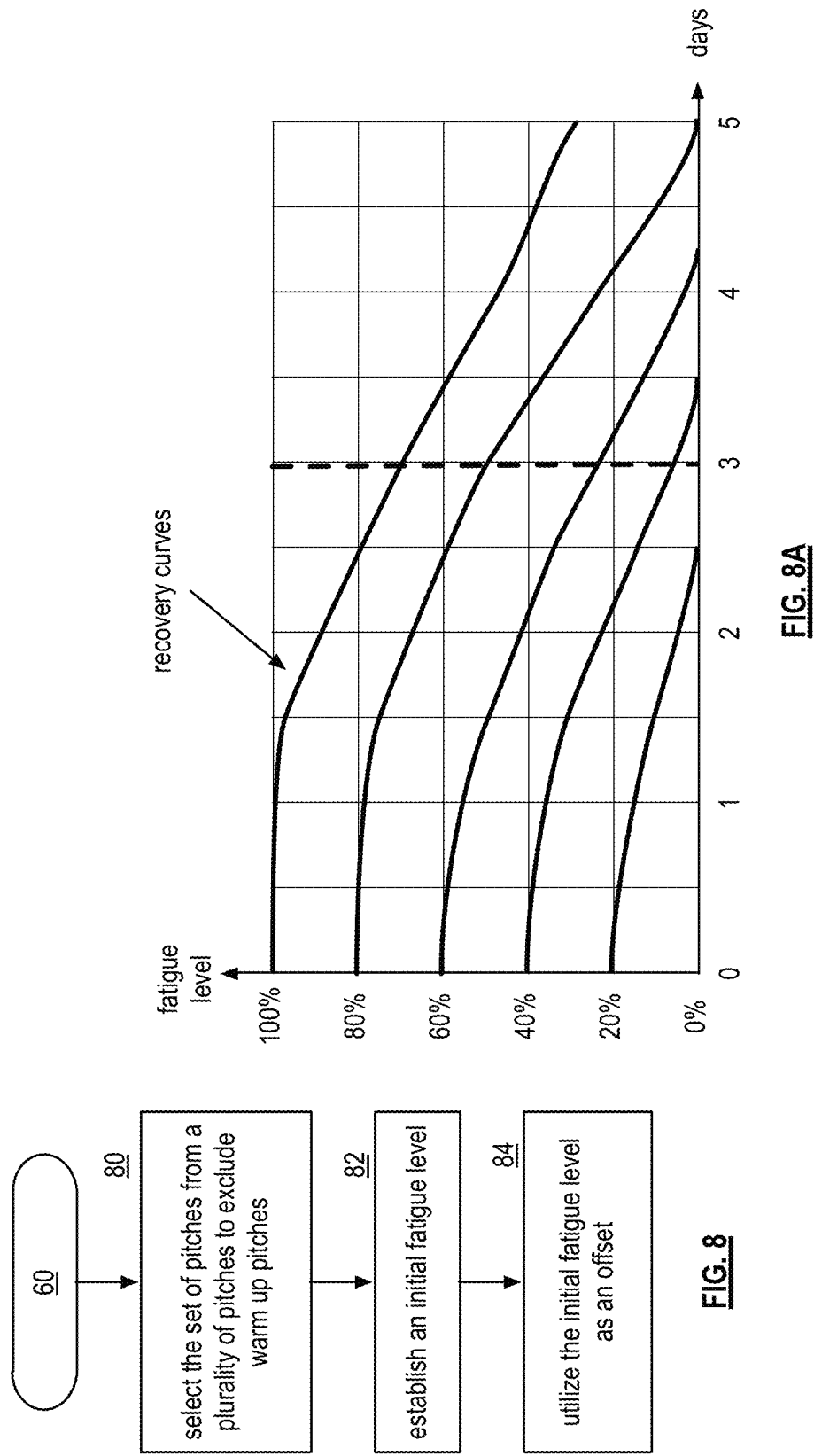

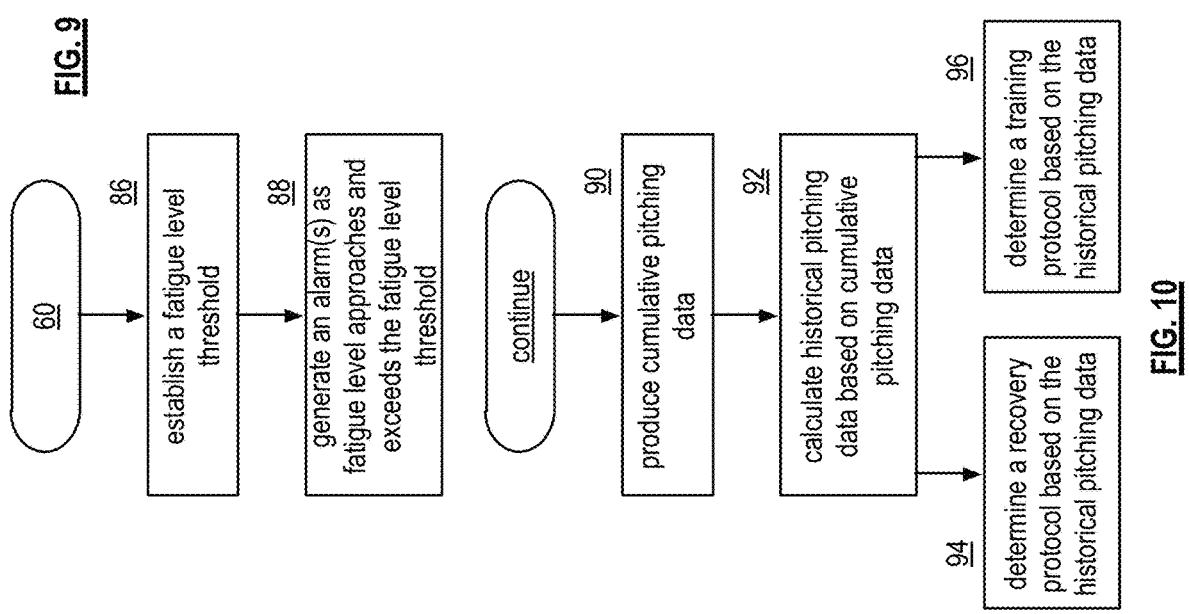

front view side view

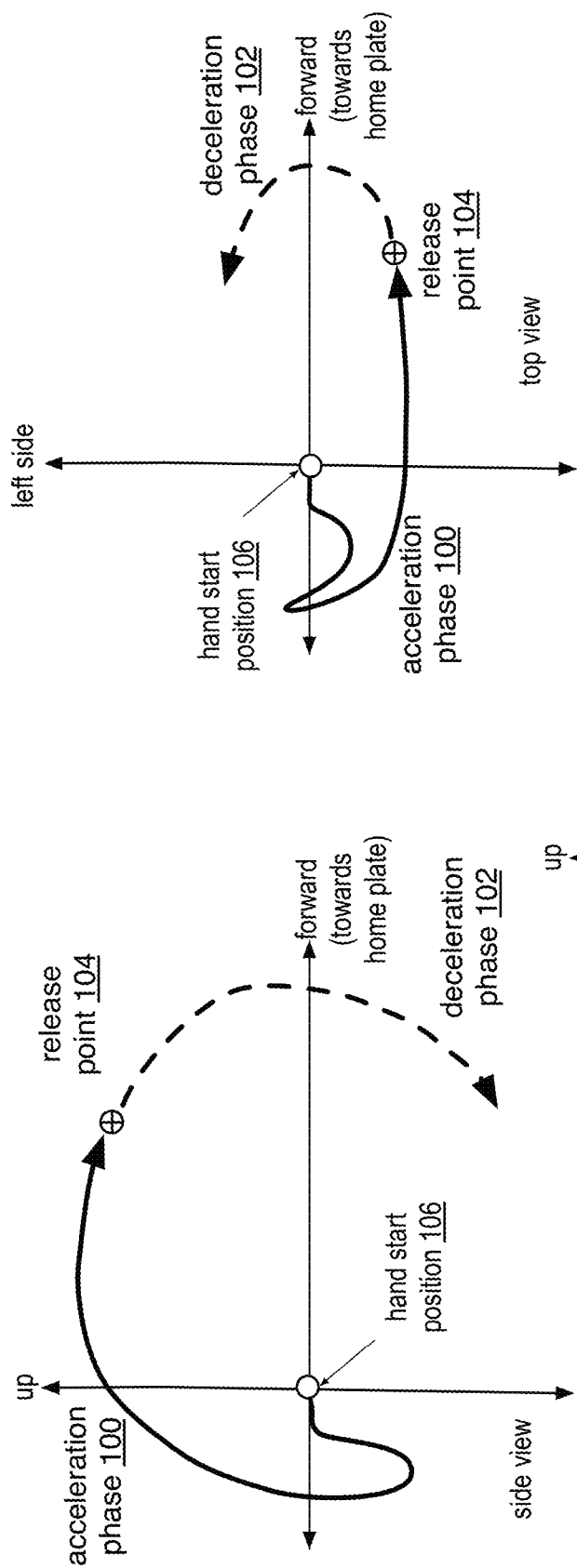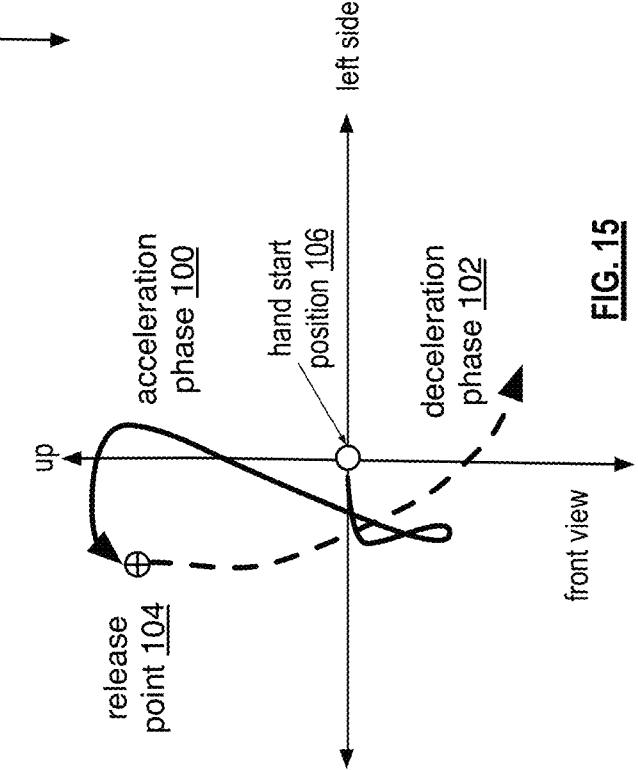
FIG. 14
FIG. 15
FIG. 13

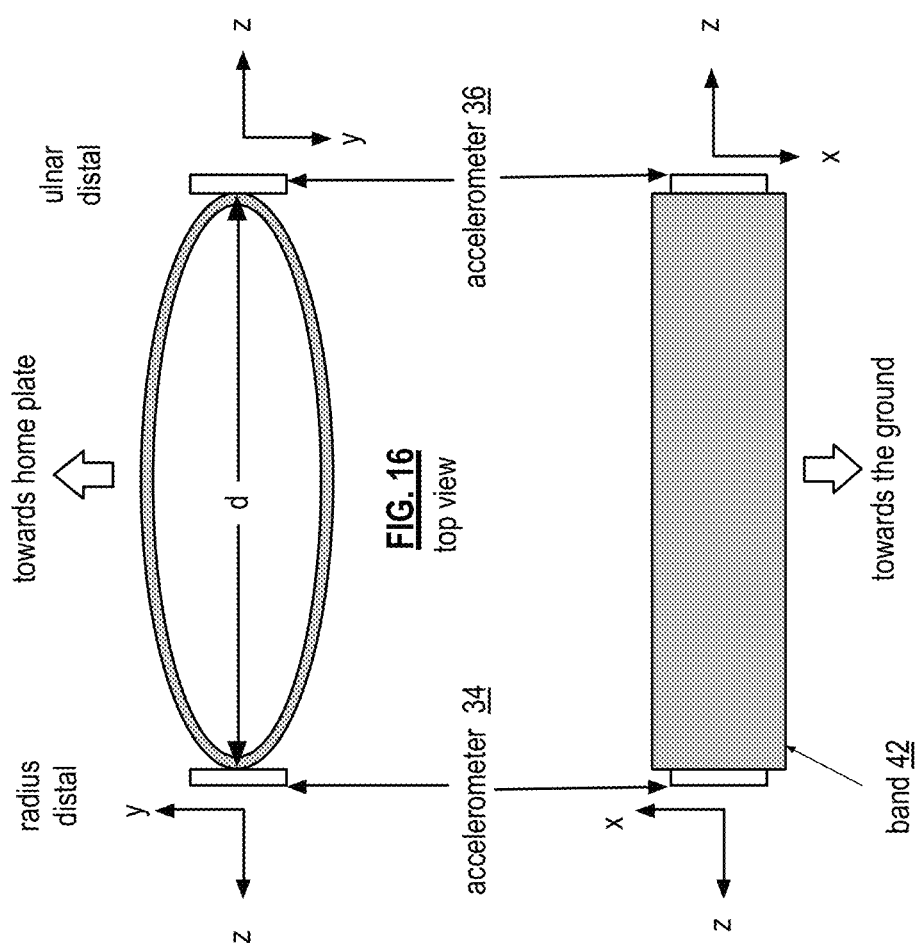

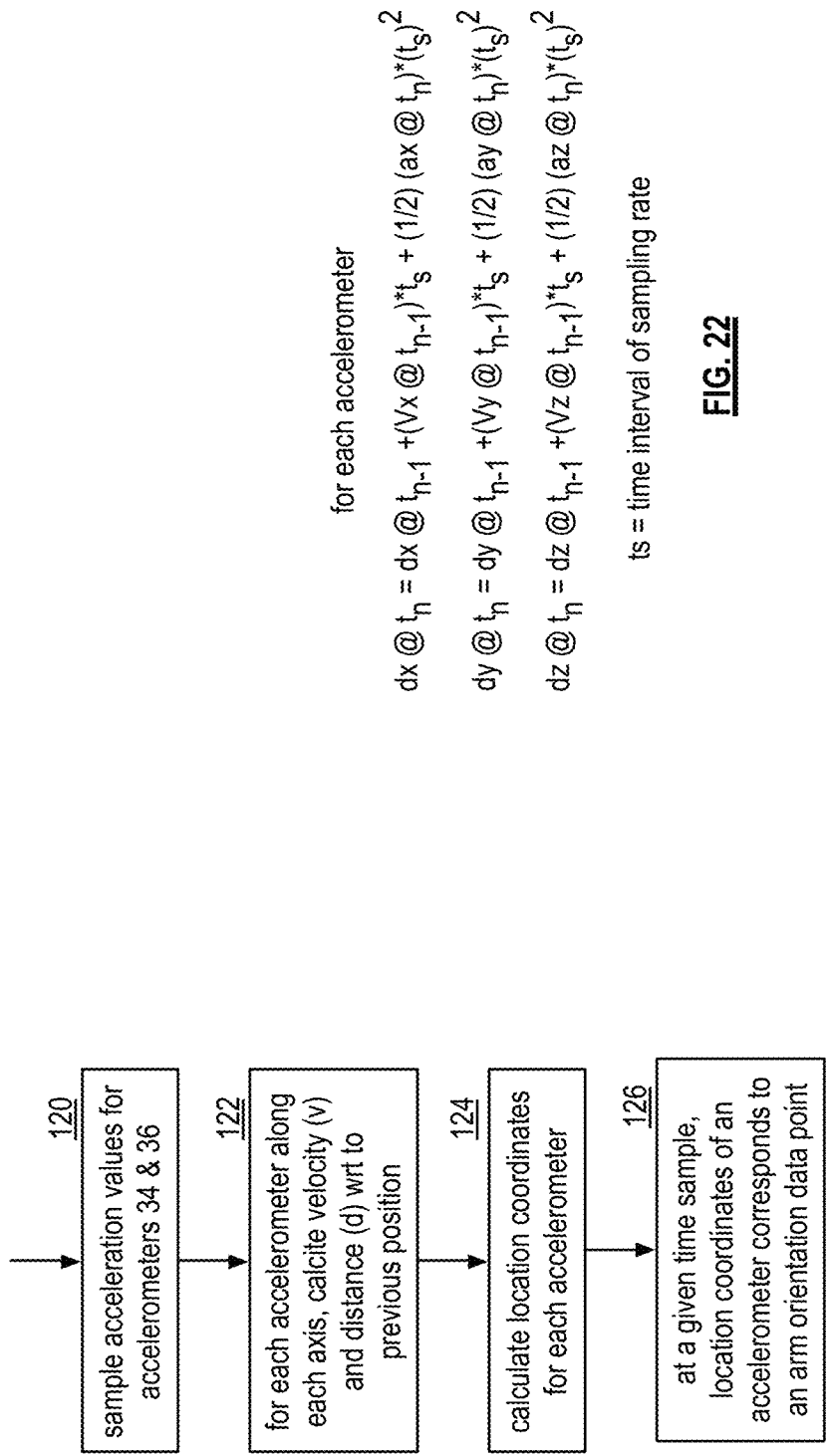

for each accelerometer $$dx @ t_n = dx @ t_{n-1} + (Vx @ t_{n-1})*t_s + (1/2)(ax @ t_n)*(t_s)^2$$
$$dy @ t_n = dy @ t_{n-1} + (Vy @ t_{n-1})*t_s + (1/2)(ay @ t_n)*(t_s)^2$$
$$dz @ t_n = dz @ t_{n-1} + (Vz @ t_{n-1})*t_s + (1/2)(az @ t_n)*(t_s)^2$$

ts = time interval of sampling rate

FIG. 22

120 — sample acceleration values for accelerometers 34 & 36

122 — for each accelerometer along each axis, calcite velocity (v) and distance (d) wrt to previous position 124 — calculate location coordinates for each accelerometer 126 — at a given time sample, location coordinates of an accelerometer corresponds to an arm orientation data point

FIG. 21 for one axis of an accelerometer $$d @ t_n = d @ t_{n-1} + (V @ t_{n-1})*t_s + (1/2)(a @ t_n)*(t_s)^2$$

$$V @ t_{n-1} = V @ t_{n-2} + (ax @ t_{n-1})*t_s$$

| | receive | calculate | | |
|---|---|---|---|---|
| | $a@t_n$ | $V@t_{n-1}$ | $d@t_{n-1}$ | $d@t_n$ |
| t0 | $a@t_0$ | 0 | 0 | $d@t_0$ ← initial position per fig 19 |
| t1 | $a@t_1$ | $= V@t_{-1} + a@t_0*ts$ | $d@t_0$ | $d@t_1$ |
| t2 | $a@t_2$ | $= V@t_0 + a@t_1*ts$ | $d@t_1$ | $d@t_2$ |
| t3 | $a@t_3$ | $= V@t_1 + a@t_2*ts$ | $d@t_2$ | $d@t_3$ |
| t4 | $a@t_4$ | $= V@t_2 + a@t_3*ts$ | $d@t_3$ | $d@t_4$ |
| t5 | $a@t_5$ | $= V@t_3 + a@t_4*ts$ | $d@t_4$ | $d@t_5$ |
| t6 | $a@t_6$ | $= V@t_4 + a@t_5*ts$ | $d@t_5$ | $d@t_6$ |
| t7 | $a@t_7$ | $= V@t_5 + a@t_6*ts$ | $d@t_6$ | $d@t_7$ ← one coordinate point of an arm orientation point |

FIG. 23

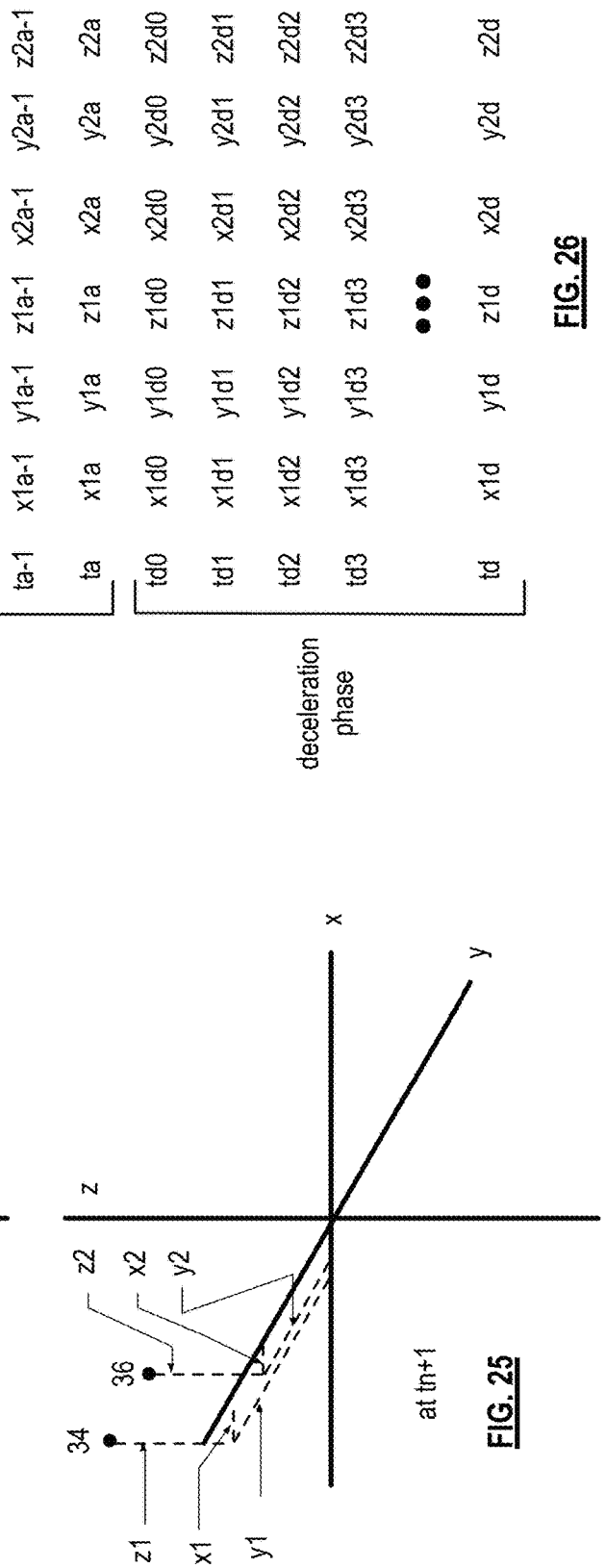
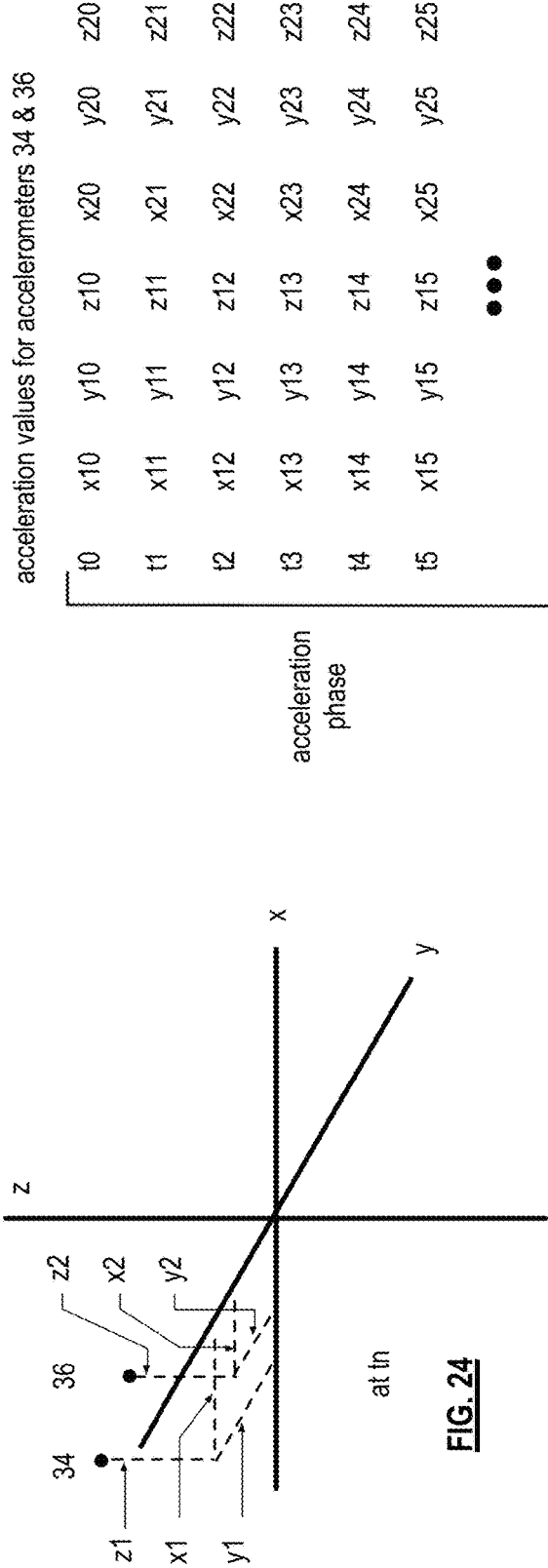

top view
cross section of wrist top view
cross section of wrist

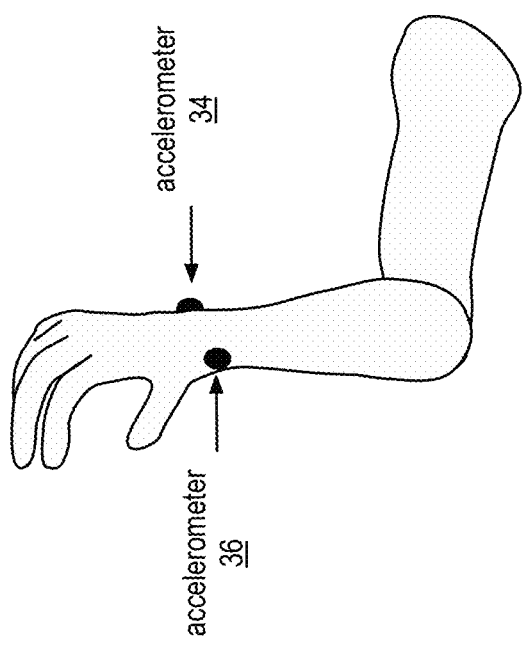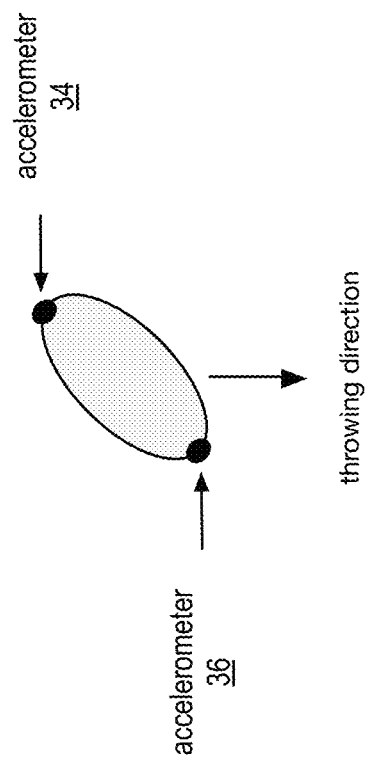

ARM FATIGUE ANALYSIS SYSTEM

CROSS REFERENCE TO RELATED PATENTS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

Technical Field of the Invention

This invention relates generally to athletic monitoring equipment and more particularly to a method of determining fatigue of a pitcher.

Description of Related Art

Wearable technology is being used more and more in sports to collect data regarding an athlete's performance of an athletic move. For instance, Motus recently introduced an arm sleeve to be worn by baseball pitchers to determine arm speed, pitch count, arm stress, arm slot, and shoulder rotation.

BRIEF DESCRIPTION OF THE SEVERAL VIEWS OF THE DRAWING(S)

FIG. 8 is a logic diagram of an example method for a portion of determining arm fatigue of a pitcher in accordance with the present invention;

FIG. 8A is a diagram of an example a fatigue level recovery curve in accordance with the present invention;

FIG. 9 is a logic diagram of an example method for a portion of determining arm fatigue of a pitcher in accordance with the present invention;

FIG. 9A is a diagram of an example a fatigue level curve versus number of pitches in accordance with the present invention;

FIG. 10 is a logic diagram of an example method for a further portion of determining arm fatigue of a pitcher in accordance with the present invention;

FIGS. 13-15 are planar views of an example of an arm path during a baseball throwing motion;

FIG. 16 is a top view diagram of another embodiment of a wrist unit in accordance with the present invention;

FIG. 17 is a front view diagram of another embodiment of an arm fatigue analysis system in accordance with the present invention;

FIG. 21 is a logic diagram of an example method for determining arm orientation data points in accordance with the present invention;

FIG. 22 is a diagram of equations for an accelerometer of an arm fatigue analysis system in accordance with the present invention;

FIG. 23 is a diagram of equations for calculating arm orientation data points of an arm fatigue analysis system in accordance with the present invention;

FIGS. 24 and 25 are diagrams of examples of determining arm orientation data points of an arm fatigue analysis system in accordance with the present invention;

FIG. 26 is a diagram of an example of arm orientation data points of a pitch in accordance with the present invention;

FIGS. 28-33 are diagrams of examples of arm orientations for various pitches in accordance with the present invention.

DETAILED DESCRIPTION OF THE INVENTION

Figure 1:
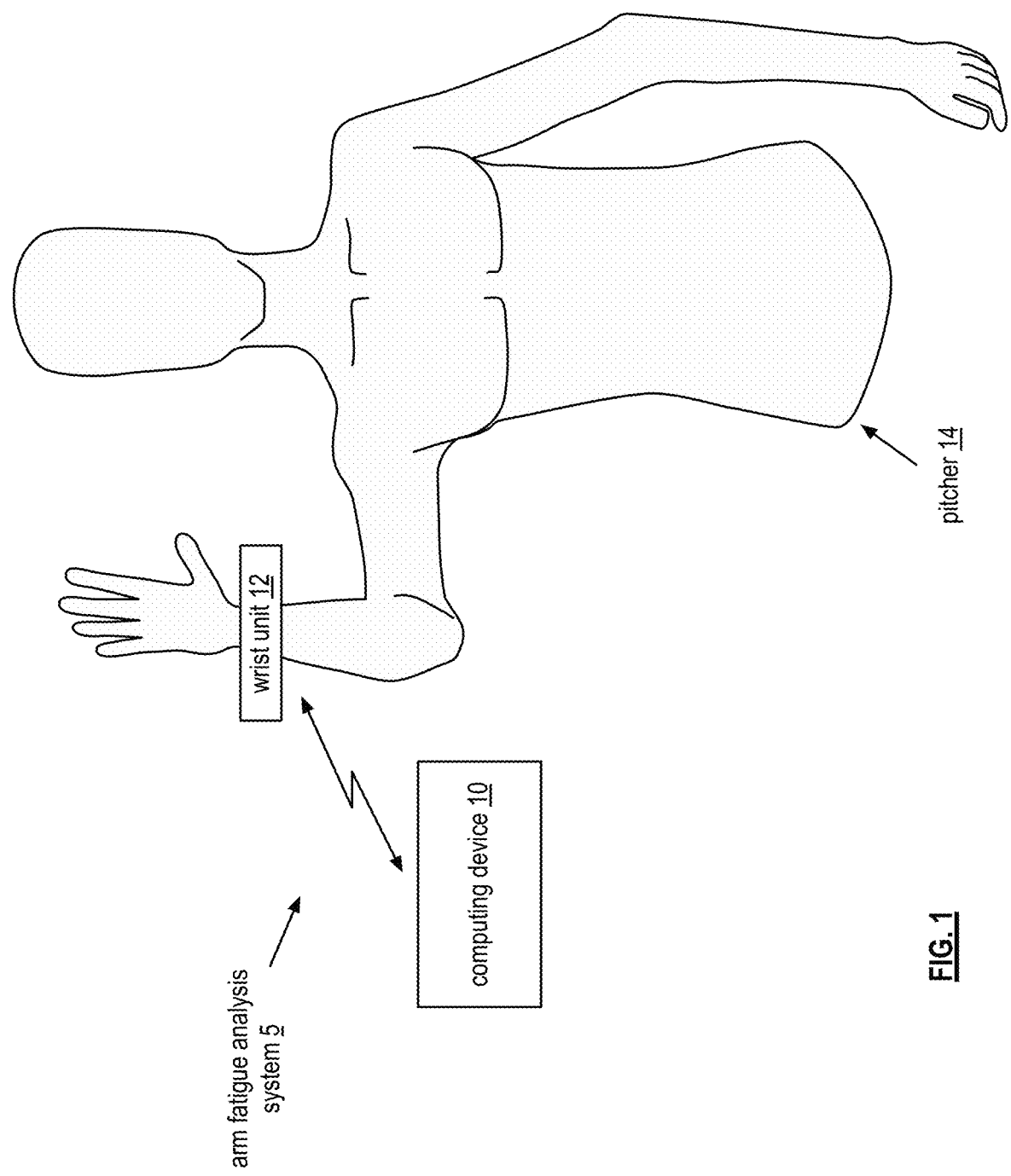
FIG. 1 is a schematic block diagram of an embodiment of an arm fatigue analysis system in accordance with the present invention.

FIG. 1 is a schematic block diagram of an embodiment of an arm fatigue analysis system 5 that includes a computing device 10 and a wrist unit 12. The computing device 10 may be cellular telephone, a computer tablet, a laptop computer, a computer, and/or any other device that includes a processing module, memory, a wireless transceiver, and a user interface.

A pitcher 14 wears the wrist unit 12 on his/her throwing arm's wrist. In general, when the pitcher 14 is throwing, the wrist unit 12 wirelessly transmits data to the computing device 10. The computing device 10, while executing operational instructions stored on a computer readable storage device (e.g., memory as subsequently defined), processes the data to determine a per pitch stress level (e.g., stress on the elbow, shoulder, forearm, legs, and/or overall body). Note that for different types of pitches (e.g., fastball, curve ball, slider, knuckle ball, changeup, slurve, knuckle-curve, screw ball, etc.) the stress level will be different. Further note that the per pitch stress level is dependent on the effort level of the pitcher 14 throwing the pitch (e.g., maximum effort will have a higher stress level than an 80% effort).

As the pitcher 14 pitches, the computing device 10 calculates a fatigue level based on the per pitch stress levels for a set of pitches. For example, the computing device 10 may include a graphical user interface (GUI) that displays the player's name, age, number, height, weight, etc. The GUI further graphically displays the pitcher's fatigue level (e.g., a graph that plots number of pitches versus energy level (e.g., 100% fully rested minus the fatigue level) or a graph that plots number of pitches versus fatigue level). The graphic may be color coded to indicate when a pitcher is becoming fatigue. For example, the graph may start out as green when the pitcher is not fatigued (i.e., energy level is high) and fades to yellow and then to red as the pitcher fatigues.

The computing device 10 may set a fatigue threshold, which indicates when the pitcher should be relieved. The fatigue threshold may be graphically displayed and/or include an alarm setting, which provides an audible alert. The computing device 10 may store, locally or remotely, the pitchers' data from game to game and practice to practice. The computing device 10 uses the accumulated data to generate historical data regarding the pitcher's maximum effort level, recovery time, training program, pre-game energy level (e.g., not fully recovered from last outing), and/or other data regarding the health of the pitcher. The computing device 10 further uses the accumulated data to generate pitching historical data (e.g., types of pitches thrown, percentage of different types of pitches thrown, etc.).

Figure 2:
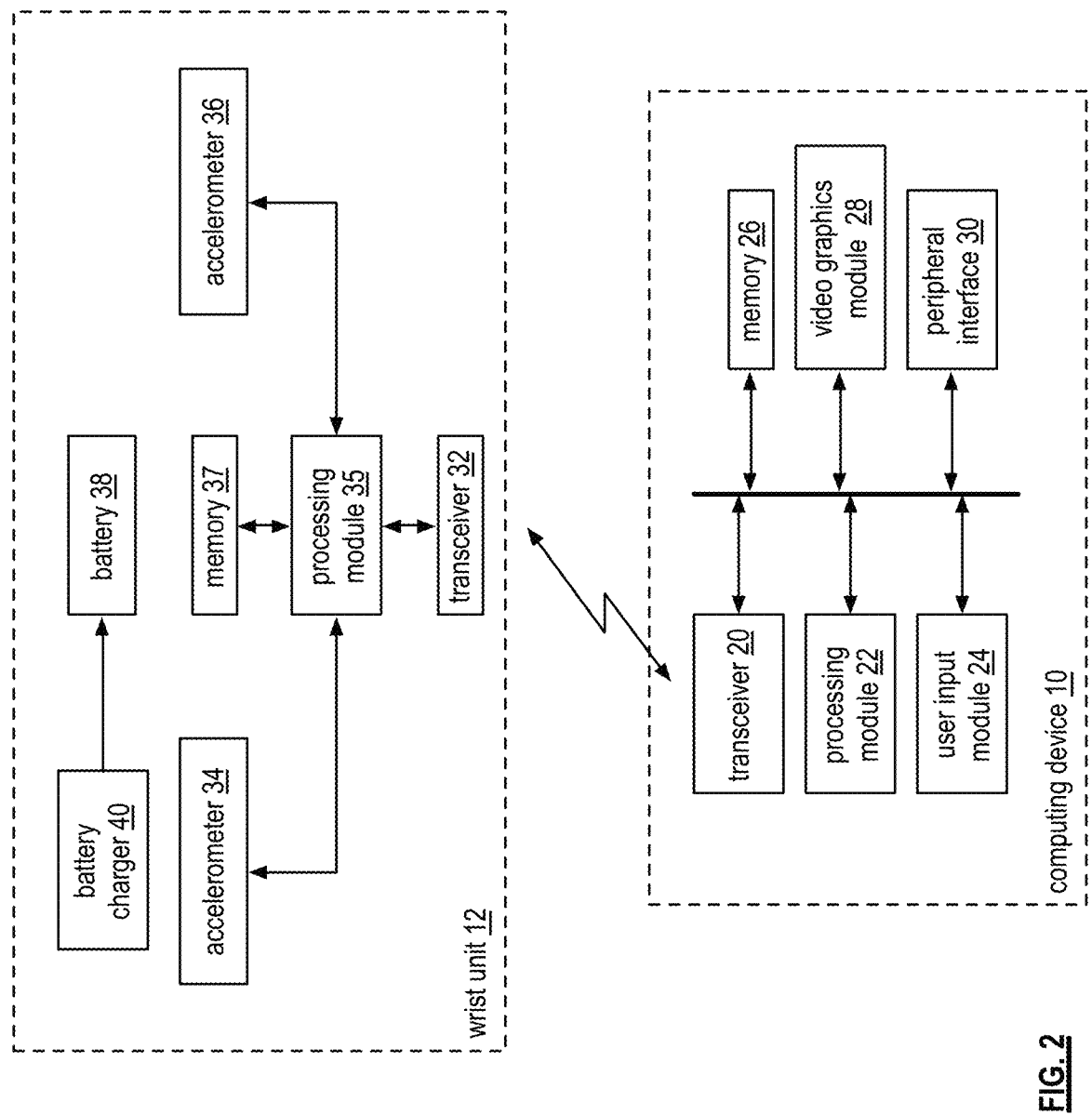
FIG. 2 is a schematic block diagram of another embodiment of an arm fatigue analysis system in accordance with the present invention.

FIG. 2 is a schematic block diagram of another embodiment of an arm fatigue analysis system 5 that includes the computing device 10 and the wrist unit 12. The computing device 10 includes a transceiver 20 (e.g., Bluetooth, ZigBee, WLAN, cellular, etc.), a processing module 22, a user input module 24 (e.g., keypad, touch screen, etc.), memory 26 (e.g., read only memory, random access memory, hard drive, solid state, cloud storage, etc.), a video graphics module 28 (e.g., a processing module for video graphics processing coupled to a video display), and a peripheral interface 30 for coupling to one or more peripheral devices (e.g., hard drive, USB interface, network interface, flash drive interface, cloud storage interface, etc.).

The wrist unit 12 includes a transceiver 32 (e.g., Bluetooth, ZigBee, WLAN, cellular, etc.), accelerometers 34 and 36, a processing module 35, memory 37 (e.g., RAM, ROM, EEPROM, etc.), a battery 38, and a battery charger 40.

In an example of operation, when the wrist unit 12 is on a pitcher's wrist and the pitcher is in the process of throwing, the accelerometers 34 and 36, which are on the radius distal and ulnar distal of the wrist, send x, y, z data to the processing module 35. At a sampling interval (e.g., sampling period of 0.1 milliseconds, or less, to 0.5 milliseconds, or more), the processing module 35 processing the x, y, z data of the accelerometers 34 and 36 into packets that are transmitted to the computing device 10 via the transceiver 32.

The transceiver 20 of computing device 10 receives the packets and de-packetizes to recapture the x, y, z data. The processing module 22 processes the x, y, z data to determine a release point arm orientation and an effort level. The processing module 22 then calculates a per pitch stress level based on the release point arm orientation and the effort level. The processing module may further calculate, for a set of pitches, a fatigue level based on the per pitch stress level of each pitch of the set of pitches.

Figure 3:
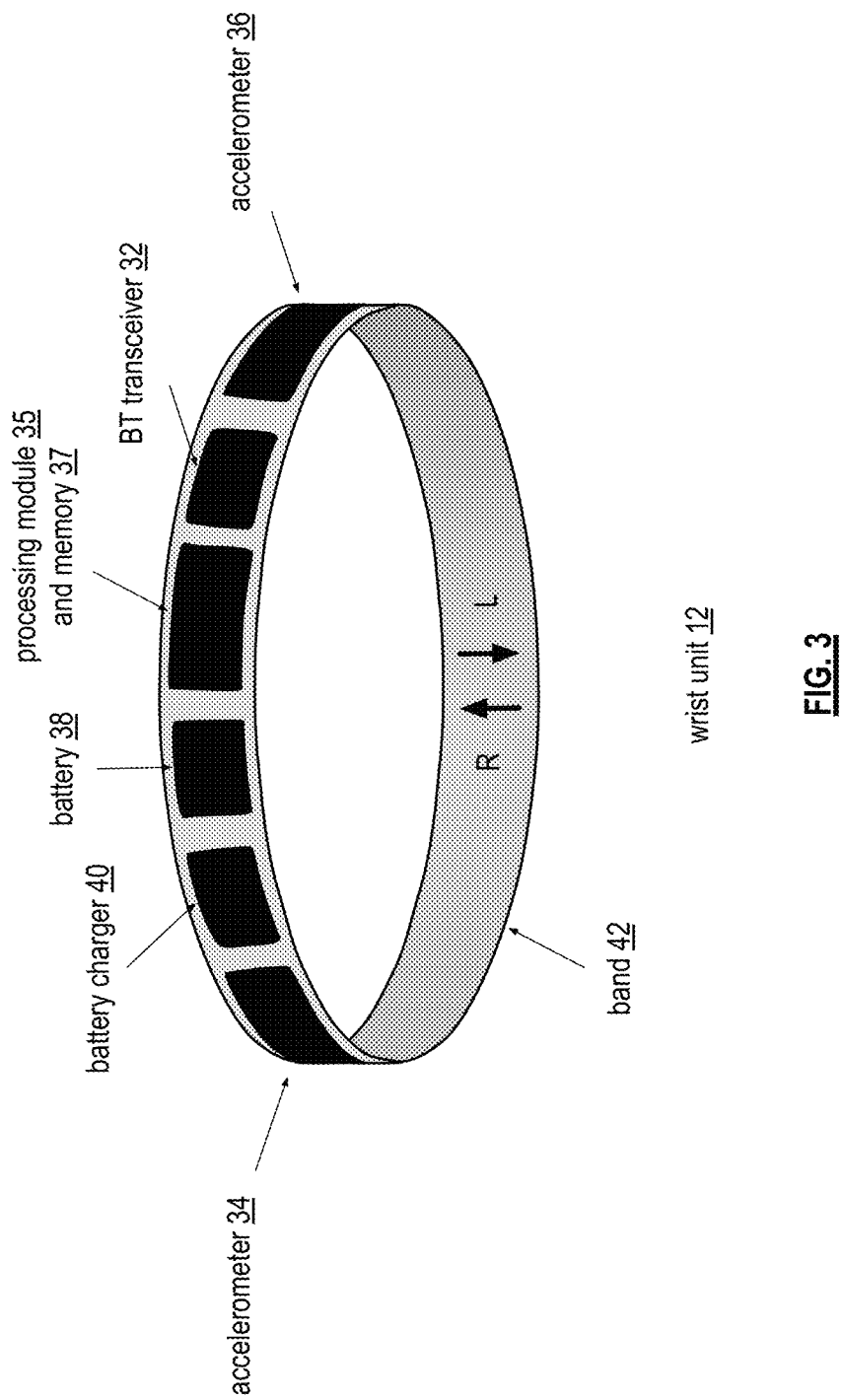
FIG. 3 is a schematic block diagram of another embodiment of an arm fatigue analysis system in accordance with the present invention.

FIG. 3 is a schematic block diagram of another embodiment of an arm fatigue analysis system that includes the transceiver 32, the accelerometers 34 and 36, the processing module 35, the memory 37, the battery 38, the battery charger 40, and a band 42. The band 42 may be comprised of a flexible and/or expandable material such as rubber, a silicon compound, neoprene, spandex, etc. The band 42 may be fabricated in different sizes to accommodate different sized pitchers. Alternatively, or in addition to, the band 42 may include a buckle and a set of holes to adjust the size.

The band 42 may be fabricated using different colored materials to match skin tone, uniform colors, etc. Further, the band 42 may include left ("L") and right ("R") indicators such that accelerometer 34 is always on the radial distal "bump" of the wrist. Note that the band 42 needs to fit securely to the wrist so that it has very little movement with respect to the movement of the wrist during a pitch. It is desired that the wrist unit 12 weigh less than a few ounce and preferably under an ounce.

Figure 4:
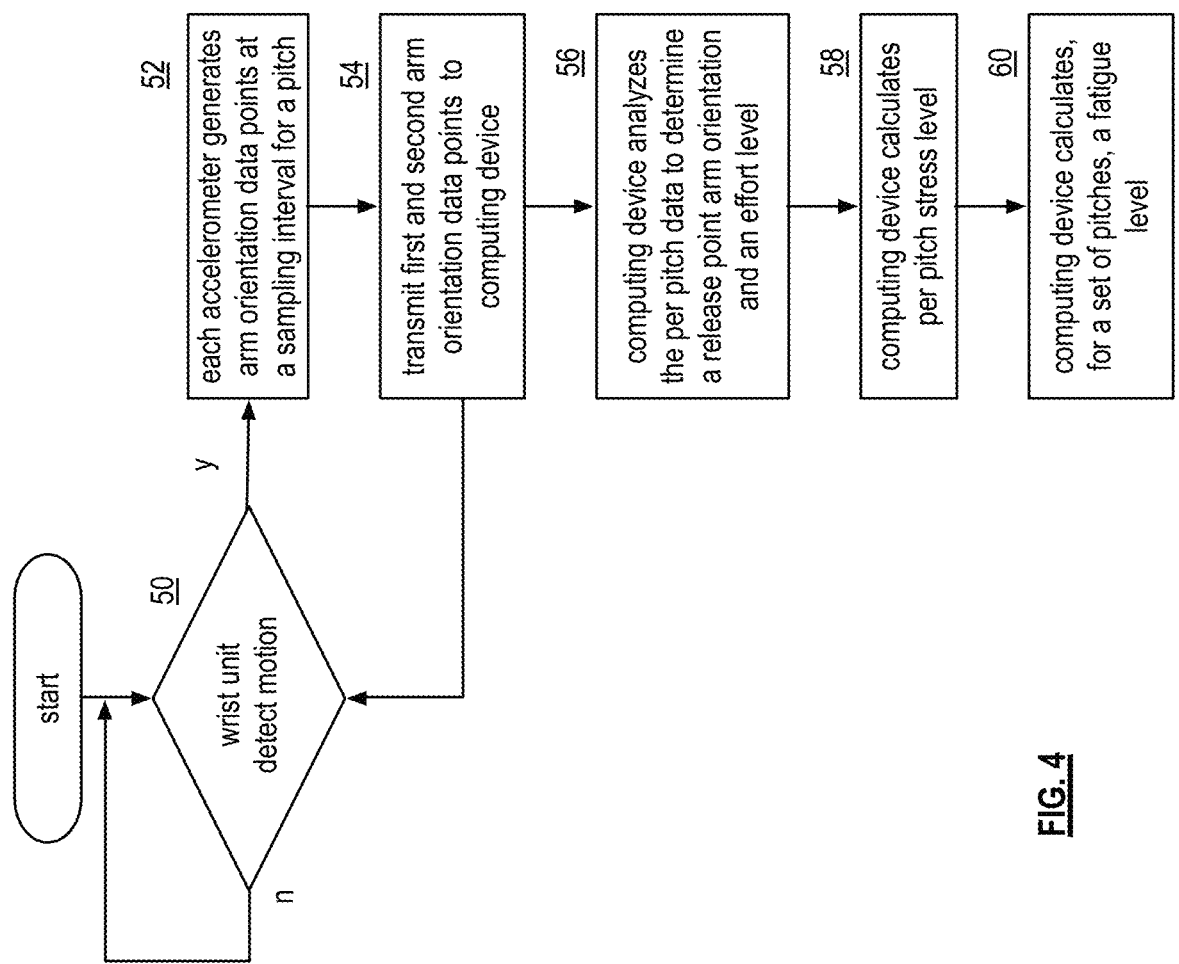
FIG. 4 is a logic diagram of an example method for determining arm fatigue of a pitcher in accordance with the present invention.

FIG. 4 is a logic diagram of example method for determining arm fatigue of a pitcher. The method begins at step 50 where the wrist unit detects motion. This may be done in a variety of ways. For example, when the wrist unit 12 in enabled (e.g., powered on via a switch to couple the battery to the other circuitry of the wrist unit), it is deemed to have detected motion. As another example, the processing module 35 may receive x, y, z data from the accelerometers 34 and 36, calculate a distance traveled over a period of time, and determine that the pitcher has not yet started a pitch (i.e., motion is not detected).

When motion is detected, the method continues at step 52 where each accelerometer generates arm orientation data points at a sampling interval for a pitch. For example, the sampling interval may be once every 0.1 milliseconds to 0.5 milliseconds (e.g., for a 100 mph pitch, the ball and hence the hand, is moving at 146.67 feet per second, 0.014467 feet per 0.1 milliseconds, or about ⅙ of an inch per 0.1 milliseconds).

At each sampling point, the processing module obtains (e.g., reads, receives, requests, etc.) the x, y, z data from each of the accelerometers 34 and 36. At a sampling point, the x, y, z data of accelerometer 34 constitutes one arm orientation data point and the x, y, z data of accelerometer 36 constitutes another arm orientation data point. Over a plurality of sampling points for a pitch, the x, y, z data of accelerometer 34 (e.g., a first sensor), which is on the radius distal area of the wrist, constitutes a plurality of first arm orientation data points and the x, y, z data of accelerometer 36 (e.g., a second sensor), which is on the ulnar distal area of the wrist, constitutes a plurality of second arm orientation data points.

The method continues at step 54 where the wrist unit 12 packetizes the arm orientation data points in accordance with a wireless communication protocol (e.g., Bluetooth) and sends them to the computing device 10. The computing device 10 collects (e.g., receives and stores), for a pitch, per pitch data that includes a plurality of first arm orientation data points and a plurality of second arm orientation data points.

The method continues at step 56 where the computing device analyzes the per pitch data to determine a release point arm orientation and an effort level. This will be discussed in greater detail with reference to FIGS. 5, 6, and one or more of FIGS. 11-33.

The method continues at step 58 where the computing device calculates a per pitch stress level based on the release point arm orientation and the effort level. This will be discussed in greater detail with reference to FIG. 7 and one or more of FIGS. 11-33.

The method continues at step 60 where the computing device calculates, for a set of pitches, a fatigue level based on the per pitch stress level of each pitch of the set of pitches. This will be discussed in greater detail with reference to FIGS. 8, 9, and one or more of FIGS. 11-33.

Figure 5:
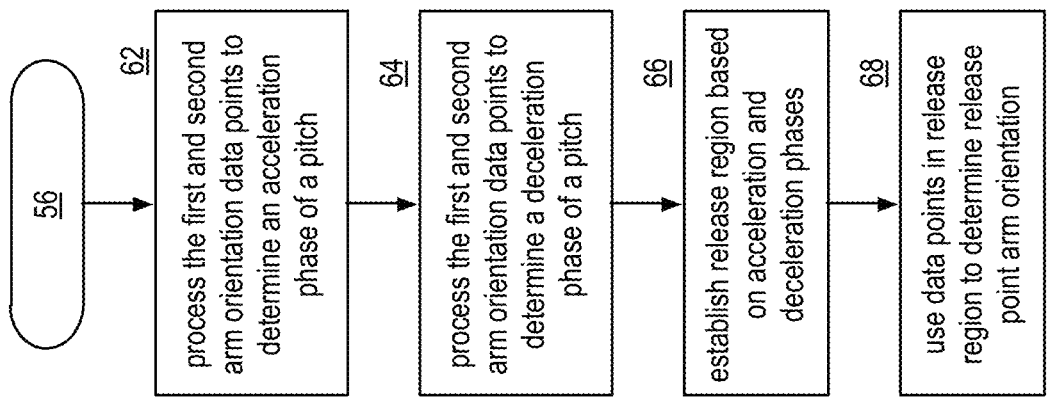
FIG. 5 is a logic diagram of an example method for a portion of determining arm fatigue of a pitcher in accordance with the present invention.

FIG. 5 is a logic diagram of a method for analyzes the per pitch data to determine a release point arm orientation and an effort level of step 56 of FIG. 4. This method begins at step 62 where the computing device processes the plurality of first and second arm orientation data points to determine an acceleration phase of the pitch. This method continues at step 64 where the computing device processes the plurality of first and second arm orientation data points to determine a deceleration phase of the pitch. Determining the acceleration phase and the deceleration phase of a pitch will be discussed in greater detail with reference to one or more of FIGS. 11-33.

This method continues at step 66 where the computing device establishes a release region of the pitch based on the acceleration phase of the pitch and the deceleration phase of the pitch. The release region may be within a few inches to a foot of the actual release point. Determining the release region of a pitch will be discussed in greater detail with reference to one or more of FIGS. 11-33.

The method continues at step 68 where the computing device uses data points of the plurality of first and second arm orientation data points corresponding to the release region of the pitch to determine the release point arm orientation. Determining the release point arm orientation of a pitch will be discussed in greater detail with reference to one or more of FIGS. 11-33.

Figure 6:
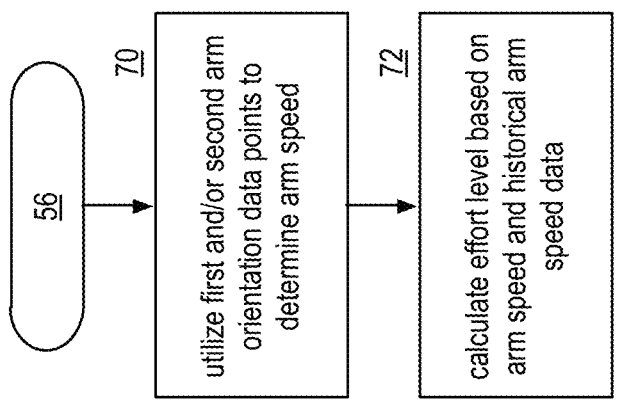
FIG. 6 is a logic diagram of an example method for a portion of determining arm fatigue of a pitcher in accordance with the present invention.

FIG. 6 is a logic diagram of a method for analyzes the per pitch data to determine a release point arm orientation and an effort level of step 56 of FIG. 4. This method begins at step 70 where the computing device utilizes the plurality of first arm orientation data points and/or the plurality of second arm orientation data points to determine an arm speed for the pitch. For example, a series of arm orientation data points (e.g., first and/or second) surrounding the release point are used to determine the arm speed at the release of the pitch.

This method continues at step 72 where the computing device calculates the effort level based on the arm speed for the pitch and historical arm speed data of a pitcher throwing the pitch. Determining the effort level of a pitch will be discussed in greater detail with reference to one or more of FIGS. 11-33.

Figure 7:
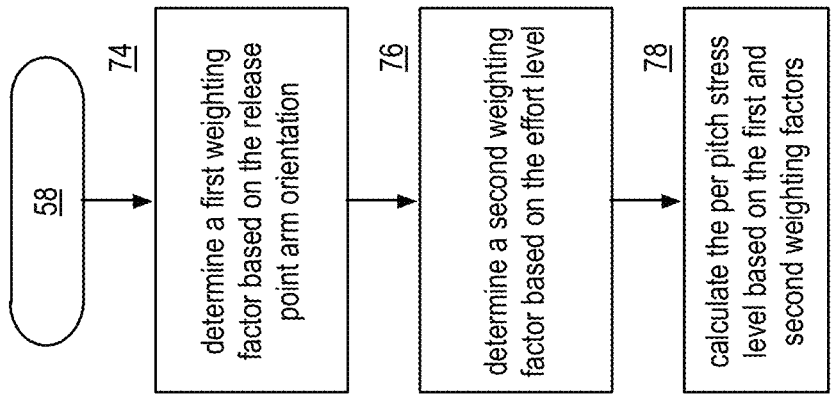
FIG. 7 is a logic diagram of an example method for a portion of determining arm fatigue of a pitcher in accordance with the present invention.

FIG. 7 is a logic diagram of a method for calculates the per pitch stress level of step 58 of FIG. 4. This method begins at step 74 where the computing device determines (e.g., looks up, calculates, etc.) a first weighting factor based on the release point arm orientation. For example, when the release point arm orientation has a line between the radius distal and ulnar distal areas of the wrist substantially parallel to home plate (which corresponds to a fastball or a changeup), then there is a first value (e.g., 1) for the first weighting factor.

As another example, when the release point arm orientation has a line between the radius distal and ulnar distal areas of the wrist is not parallel to home plate and with the ulnar distal area more towards home plate (which corresponds to a curveball or a slider), then there is a second value (e.g., 1.5) for the first weighting factor. This second value may further be scaled based on the angle of the line between radius distal and ulnar distal areas of the wrist and the front edge of home plate. For instance, the second value equals 1 plus the angle divided by 90 (e.g., for a 45 degree angle, the second value=1+45/90, or 1.5).

As another example, when the release point arm orientation has a line between the radius distal and ulnar distal areas of the wrist is not parallel to home plate and with the radius distal area more towards home plate (which corresponds to a screwball), then there is a third value (e.g., 1.75) for the first weighting factor. This third value may further be scaled based on the angle of the line between radius distal and ulnar distal areas of the wrist and the front edge of home plate. For instance, the second value equals 1.25 plus the angle divided by 90 (e.g., for a 45 degree angle, the second value=1.25+45/90, or 1.75).

The method continues at step 76 where the computing device determines a second weighting factor based on the effort level. The second weighting factor may be calculated, looked up, etc. to be a normalized representation of the effort level. For example, from historical data, the maximum arm speed of a pitcher can be determined. When the arm speed for the current pitch substantially matches the maximum arm speed, then it can be determined that the effort level is 100%. This may be normalized to a value of 1.0. When the arm speed for the current pitch is less than the maximum arm speed, then it can be determined that the effort level is below 100% (e.g., 90%). This may be normalized to a value of 0.9.

This method continues at step 78 where the computing device calculates the per pitch stress level based on the first and second weighting factors. For example, a mathematical function is performed on the first and second weighting factors to produce the per pitch stress level. The mathematical function may be a linear function such as addition or multiplication and/or a non-linear function such exponential equation, a quadratic equation, etc. As a specific example, assume that the first weighting factor is a value of 1.45 and the second weighting factor is a value of 0.89, then the per pitcher stress level is 0.89*1.45=1.29.

FIG. 8 a logic diagram of a method for calculates the fatigue level of step 60 of FIG. 4. This method begins at step 80 where the computing device selects the set of pitches from a plurality of pitches to exclude warm-up pitches (e.g., an arm orientation of a fastball with 60% or less of maximum effort). This may be done on a pitch-by-pitch basis to determine whether the per pitch data for a pitch indicates a warm-up pitch. When, for a pitch, the per pitch data does not indicate a warm-up pitch, including the pitch in the set of pitches.

This method continues at step 82 where the computing device establishes an initial fatigue level for a pitcher. This may be done in a variety of ways. For example, the historical data of the pitcher may be analyzed to determine his recovery time, the last time the pitcher pitched, to what fatigue level did the pitcher pitch to, etc. As a specific example and with reference to FIG. 8A, assume that the fatigue level ranges from 0% fatigued (i.e., fully rested and recovered) to 100% fatigued (i.e., loss of arm speed, loss of control, pitching mechanics broken down, and/or other factors). Further assume that, for a pitcher, he/she needs various time frames from reaching various fatigue levels from the day he/she last pitched (which is day 0 on the chart). Note that the recovery curves may be individualized for a given player to take into account his/her own unique physical and recovery characteristics. Further note the curves and/or the initial fatigue level may be determined using a sinusoidal function of the fatigue level on day 0 and days since last pitched.

At day 3 after last pitching, the pitcher is fully recovered if he/she reached a fatigue level of about 30% during the last outing; is about 90% recovered (i.e., an initial fatigue level of 10%) if he/she reached a fatigue level of about 40% during the last outing; is about 80% recovered (i.e., an initial fatigue level of 20%) if he/she reached a fatigue level of about 60% during the last outing; and is about 50% recovered (i.e., an initial fatigue level of 50%) if he/she reached a fatigue level of about 80% during the last outing.

The computing device may further adjust the initial fatigue level based on an interpretation of the warm up pitches and/or a sampling of pitches early in the present outing (e.g., pitcher is less fatigued than initially indicated or pitcher is more fatigued than initially indicated). For example, the initial fatigue level may be 20%, but after interpreting some pitches, the fatigue level is adjusted to 25% when the sampled pitches indicate that the pitcher is more fatigued that initially determined.

Returning to the method of FIG. 8, the method continues at step 84 where the computing device utilizes the initial fatigue level as an offset when calculating the fatigue level based on the per pitch stress level of each pitch of the set of pitches. For example, if the initial fatigue level is determined to be 25%, then the calculated fatigue level is increased by 25%. As a specific example, assume that after 20 pitches, the fatigue level is calculated to be 15%, which is increased by 25% to 40%.

FIG. 9 a logic diagram of a method for calculates the fatigue level of step 60 of FIG. 4. This method begins at step 86 where the computing device establishing a fatigue level threshold. This may be done by receiving a command from a user of the system (e.g., a coach), calculating it based on historical data, and/or by determining a predictive level. Note that the computing device may generate more than one threshold. This method continues at step 88 where the computing device generates one or more alarm indicators (e.g., audible and/or visual) as the fatigue level approaches and exceeds the fatigue level threshold.

FIG. 9A is a diagram of an example a fatigue level curve versus number of pitches. The graph further includes a threshold (e.g., 75% fatigue level). As the pitcher pitches, the fatigue level increases as an accumulation of the per pitch stress level. A first alarm may be triggered when the pitcher reaches 90% of the threshold; a second alarm may be triggered when the pitcher reaches 100% of the threshold; and a third alarm may be triggered when the pitcher exceeds 100% of the threshold.

FIG. 9A further shows three fatigue level curves (#1, #2, and #3). As shown, fatigue level curve #1 reaches the threshold around 55 pitches; fatigue level curve #2 reaches the threshold around 68 pitches; and fatigue level curve #3 does not reach the threshold at 75 pitches. With the fatigue level being a culmination of per pitch stress (e.g., effort level and arm orientation at release point), the pitcher of fatigue level curve #1 is exerting a much higher per pitch stress level than pitcher of fatigue level curve #3. Accordingly, measuring the fatigue level of a pitcher is a more accurate measure of a pitcher's true fatigue level than using a pitch count.

FIG. 10 a logic diagram of further steps that may be performed in association with the method of FIG. 4. This begins at step 90 where the computing device produces cumulative pitching data. For example, the computing device accumulates the fatigue level for a plurality of sets of pitches (e.g., fatigue level for a plurality of pitching outings, each of which includes a set of pitches); the release point arm orientation for the plurality of sets of pitches; the effort level for the plurality of sets of pitches; and/or the per pitch stress level for the plurality of sets of pitches.

The method continues at step 92 where the computing device calculates historical pitching data for a pitcher based on the cumulative pitching data. For example, the historical pitching data is a tabulation of a season's worth of outings or more. The historical pitching data may be used to determine a recovery protocol based on the historical pitching data as shown in step 94 and/or to determine a training protocol based on the historical pitching data as shown in step 96.

Figure 12:
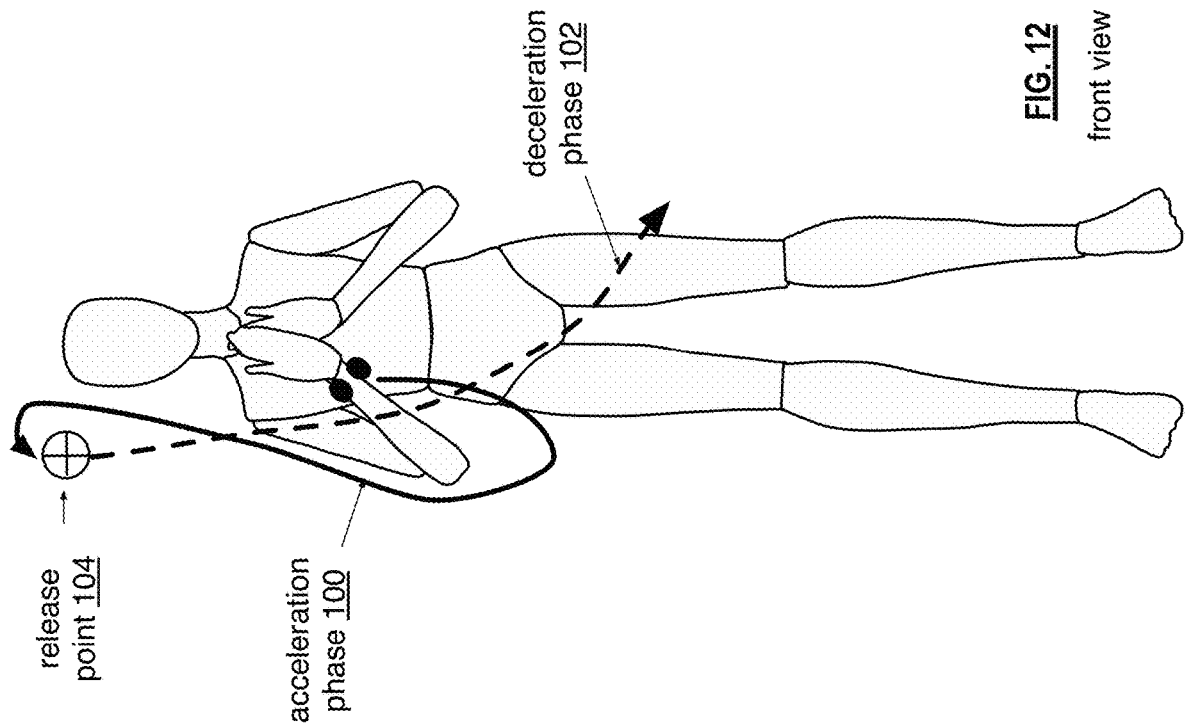
FIG. 12 is a front view of an example of an arm path during a baseball throwing motion.
Figure 11:
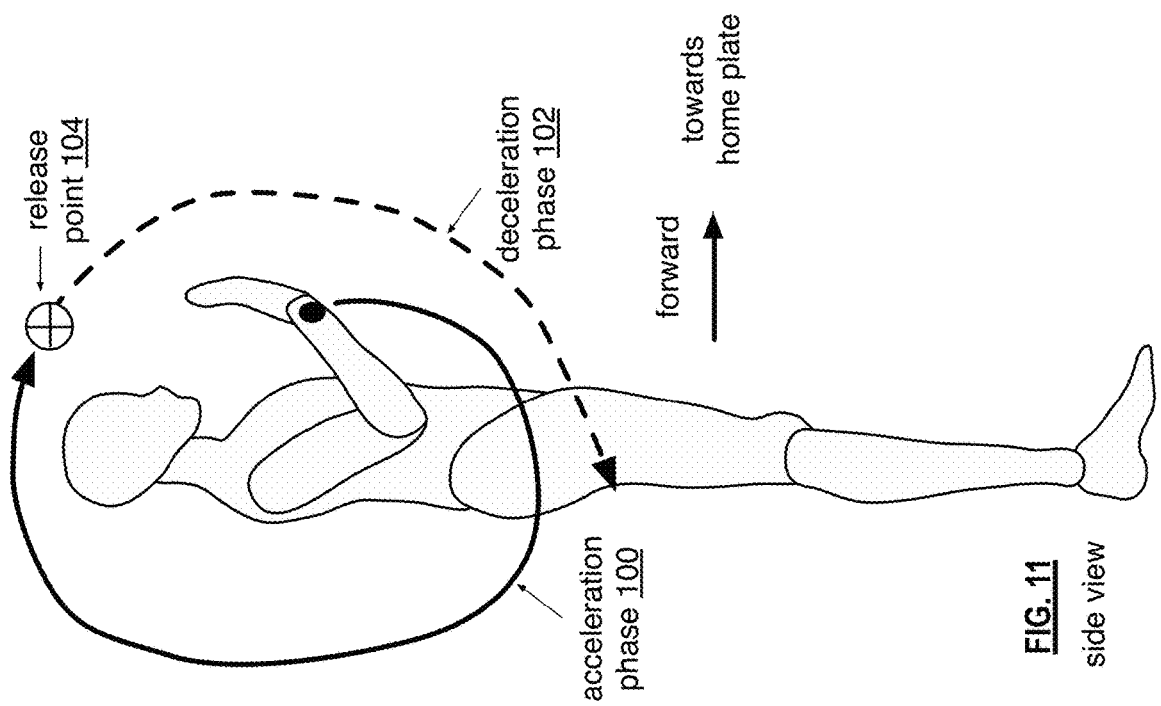
FIG. 11 is a side view of an example of an arm path during a baseball throwing motion.

FIG. 11 is a side view and FIG. 12 is a front view of an example of an arm path during a baseball throwing motion. With a pitcher facing home plate, his/hands start in an initial position (e.g., at the waist, up by the chin, etc.). When a pitcher starts his/her windup, the throwing arm traverses a three-dimensional path that includes an acceleration phase 100, a release point 104, and a declaration phase 102. Accordingly, the pitching hand is accelerating during the acceleration phase 100 and is decelerating during the deceleration phase 102. During a pitch, the elbow experiences an energy of up to 600 Newton's/meter. This energy is built up during the acceleration phase 100 and is dissipated during the deceleration phase 102.

FIGS. 13-15 are planar views of an example of an arm path during a baseball throwing motion. As shown, in each plane, the ball (and hence the pitching hand) moves from the start position 106 through the acceleration phase 100, the release point 104, and then the deceleration phase 102. The x, y, z data produced by the accelerometers 34 and 36 tracks the pitching hand movement in each of the three planes.

FIG. 16 is a top view diagram and FIG. 17 is a front view diagram of another embodiment of the wrist unit 12 with accelerometer 34 on the radius distal bump of the throwing wrist and accelerometer 36 on the ulnar distal bump of the throwing wrist. The example of this figure is for a right-handed pitcher. For a left-handed pitcher, the system would be a mirror image of that shown.

In FIG. 16, the x, y plane of accelerometer 34 is shown to have the y-axis in the direction of home plate and the z-axis to the left of the pitcher. The x, y plane of accelerometer 36 is shown to have the y-axis in the opposite direction of home plate and the z-axis to the right of the pitcher. In FIG. 17, the x, z plane of accelerometer 34 is shown to have the x-axis in the up direction and the z-axis to the left of the pitcher. The x, z plane of accelerometer 36 is shown to have the x-axis in the down direction and the z-axis to the right of the pitcher.

In this orientation and with the wrist unit 12 at rest, accelerometer 34 is providing x, y, z data of an "x" acceleration (ax34) of −9.8 m/s$^2$, a "y" acceleration (ay34) of 0 m/s$^2$, and a "z" acceleration (az34) of 0 m/s$^2$. Accelerometer 36 is providing x, y, z data of an "x" acceleration (ax36) of 9.8 m/s$^2$, a "y" acceleration (ay36) of 0 m/s$^2$, and a "z" acceleration (az36) of 0 m/s$^2$.

Figure 18:
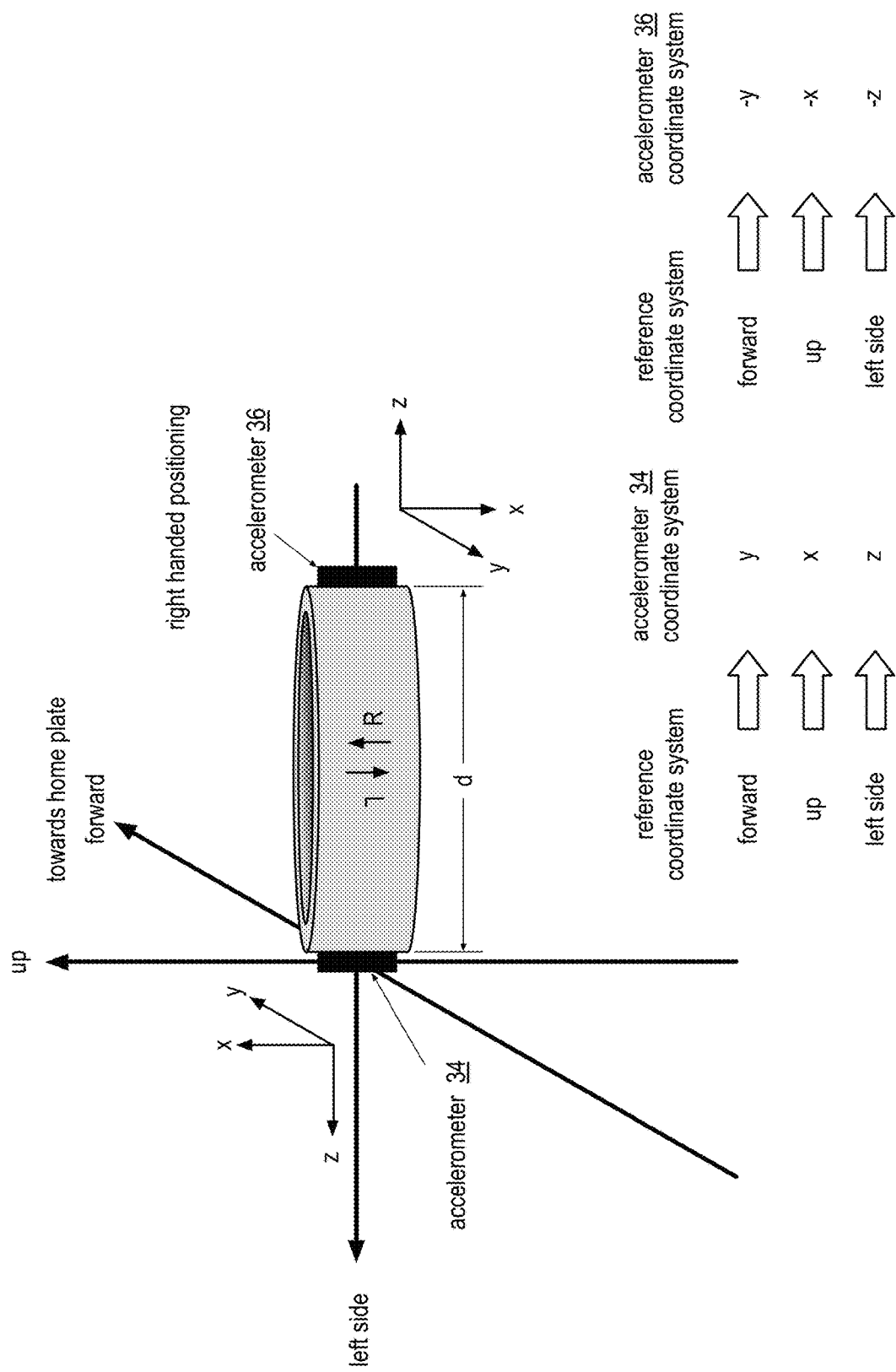
FIG. 18 is a diagram of an example of a coordinate system for an arm fatigue analysis system in accordance with the present invention.

FIG. 18 is a diagram of an example of a reference coordinate system for an arm fatigue analysis system. As shown, the reference coordinate system includes a forward axis (i.e., towards home plate), an up axis (i.e., perpendicular to the ground), and a left axis (i.e., parallel to the front edge of home plate). The coordinate system for each of the accelerometers 34 and 36 is mapped to the reference coordinate system.

In this example, the coordinate system of accelerometer 34 is mapped to the origin of the reference coordinate system. As shown, the y-axis of the coordinate system of accelerometer 34 corresponds to the forward axis of the reference coordinate system; the x-axis of the coordinate system of accelerometer 34 corresponds to the up axis of the reference coordinate system; and the z-axis of the coordinate system of accelerometer 34 corresponds to the left axis of the reference coordinate system.

As is also shown, the coordinate system of accelerometer 36 is offset from the origin of the reference coordinate system by a distance "d", which is the distance between accelerometers 34 and 36. With this offset, the y-axis of the coordinate system of accelerometer 36 corresponds to the negative forward axis of the reference coordinate system; the x-axis of the coordinate system of accelerometer 36 corresponds to the negative up axis of the reference coordinate system; and the z-axis of the coordinate system of accelerometer 36 corresponds to the negative left axis of the reference coordinate system.

Figure 19:
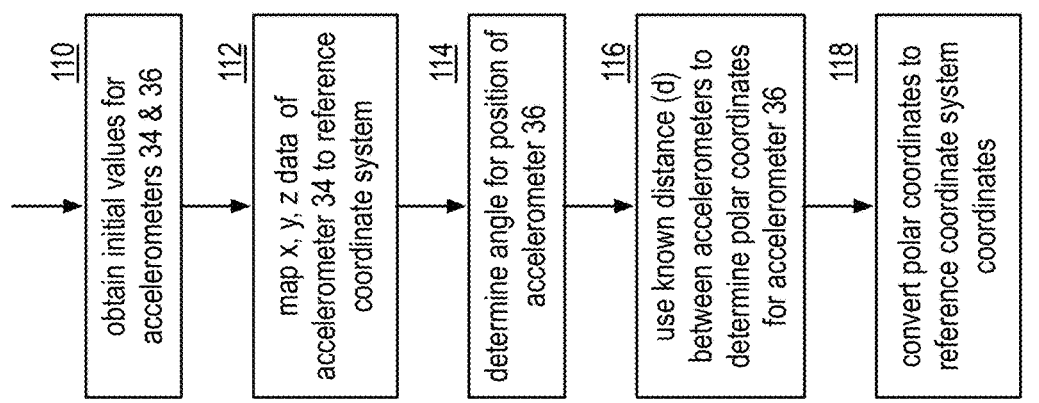
FIG. 19 is a logic diagram of an example method for determining an initial relationship between two accelerometers of an arm fatigue analysis system in accordance with the present invention.

FIG. 19 is a logic diagram of an example method for determining an initial relationship between two accelerometers of an arm fatigue analysis system prior to a pitch. The method begins at step 110 where the computing device obtains initial values (e.g., x, y, z data) from accelerometers 34 and 36. The initial values correspond to the x, y, z data the accelerometers generate just prior to the pitch commencing (e.g., at time t0). As such, initial values may be include one or more sets of x, y, z data from each of the accelerometers, where one set corresponds to one sampling interval of x, y, z data.

As an example, assume that the wrist unit 12 is on the right wrist of the pitcher and pitcher's hands are set. With this orientation of the wrist unit, accelerometer 34 provides x, y, z data of an x-axis acceleration at time t0 (ax34 @ t0) of 6.8 m/s$^2$; a y-axis acceleration at time t0 (ay34 @ t0) of −1.2 m/s$^2$; and a z-axis acceleration at time t0 (az34 @ t0) of 4.2 m/s$^2$. And accelerometer 36 provides x, y, z data of an x-axis acceleration at time t0 (ax36 @ t0) of 1.9 m/s$^2$; a y-axis acceleration at time t0 (ay36 @ t0) of −6.1 m/s$^2$; and a z-axis acceleration at time t0 (az36 @ t0) of −5.6 m/s$^2$.

Figure 20:
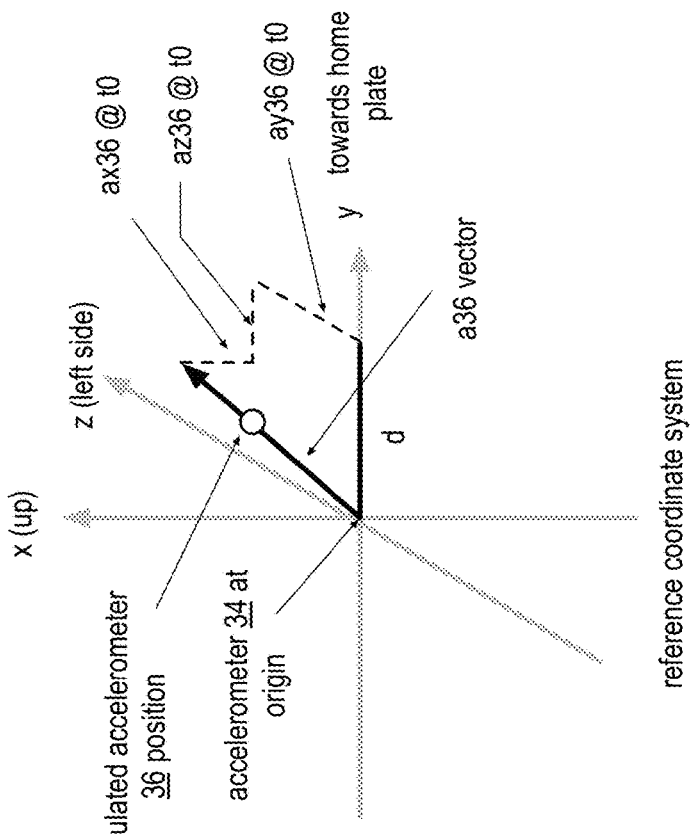
FIG. 20 is a diagram of example determining an initial relationship between two accelerometers of an arm fatigue analysis system in accordance with the present invention.

The method continues at step 112 where the computing device maps the x, y, z data of accelerometer 34 to the reference coordinate system. The method continues at step 114 where the computing device determines an angle for the position of accelerometer 36 based on the x, y, z data of accelerometer 36 at time t0. FIG. 20 illustrates an example of determining the angle of the position of accelerometer 36 based on establishing a vector for accelerometer 36 (a36 vector) from ax36 @ t0, ay36 @ t0, and az36 @ t0. The three dimensional angle of vector a36 from the origin of the reference coordinate system is the angle for accelerometer 36.

Returning to the method of FIG. 19, the method continues at step 116 where the computing device uses the known distance between the accelerometers in combination with the angle to determine polar coordinates for the initial position of accelerometer 36. The method continues at step 118 where the computing device converts the polar coordinates for the initial position of accelerometer 36 into coordinates of the reference coordinate system.

With the initial positions of the accelerometers determined, when the pitch commences, the arm orientation data points are created at a sampling interval. This may be done using the method of FIG. 21. This method begins at step 120 where the wrist units samples x, y, z data of the accelerometers at a sampling rate and provides the sampled x, y, z data to the computing device. The method continues at step 122 where the computing device calculates velocity and distance for a given set of sampled x, y, z data of the accelerometers.

For example, the computing device uses the equations as shown in FIGS. 22 and 23 to determine the distances along each axis for each of the accelerometers. In these equations, "dx" corresponds to the distance along the x-axis; "dy" corresponds to the distance along the y-axis; "dz" corresponds to the distance along the z-axis; "tn" corresponds to the current sampling interval; "tn−1" corresponds to the previous sampling interval; "ts" corresponds to the duration of a sampling interval (i.e., the sampling period); "vx" corresponds to the velocity along the x-axis; "vy" corresponds to the velocity along the y-axis; "vz" corresponds to the velocity along the z-axis; "ax" corresponds to the acceleration along the x-axis; "ay" corresponds to the acceleration along the y-axis; and "az" corresponds to the acceleration along the z-axis.

FIG. 23 further illustrates, each sampling interval (e.g., t1, t2, etc.), what data is received and what data is calculated. For example, at sampling interval t3, the computing device receives acceleration data (e.g., x, y, z data from each accelerometer) and calculates the velocity along each axis of the previous sampling interval (e.g., v@tn−1) using the equation v@tn−1=v@tn−2+(a@tn−1)*ts. The computing device then calculates the distance along each axis for the current sampling interval using the distance equation.

Returning to the discussion of FIG. 21, the method continues at step 124 where the computing device calculates the location coordinates for each of the accelerometers for the current sampling interval. FIGS. 24 and 25 illustrate an example of calculating location coordinates for the accelerometers. In FIG. 24, the coordinates for accelerometer 34 are x1, y1, z1 and the coordinates for accelerometer 36 are x2, y2, z2 at sampling interval tn. For sampling interval tn+1, having calculated the distances traveled along each axis by each accelerometer, the coordinates for the accelerometers 34 and 36 are determine by adding the calculated distances to the coordinates of at tn. FIG. 25 illustrates an example of the coordinates for accelerometer 34 are x1, y1, z1 and the coordinates for accelerometer 36 are x2, y2, z2 at sampling interval tn+1.

Returning to the discussion of FIG. 21, the method continues at step 126, the computing device equates the location coordinates of the accelerometers to the arm orientation data points for the current sampling interval. As arm orientation data points for sampling intervals are collected, the computing device processes them to determine an acceleration phase, a release region and/or release point, and a deceleration phase of a pitch.

FIG. 26 is a diagram of an example of arm orientation data points of a pitch the computing device collects and analyzes to determine the acceleration phase, the deceleration phase, and the release point. In this example, the first column corresponds to the sampling interval, where t0 is corresponds to when the pitch commences. The data points x1, y1, and z1 corresponds to x, y, z location coordinates of accelerometer 34 at the corresponding sampling interval and the data points x2, y2, and z2 corresponds to x, y, z location coordinates of accelerometer 36 at the corresponding sampling interval. Note that ta corresponds to the last sampling interval of the acceleration phase and td0 corresponds to the first sampling interval of the deceleration phase.

Figure 27:
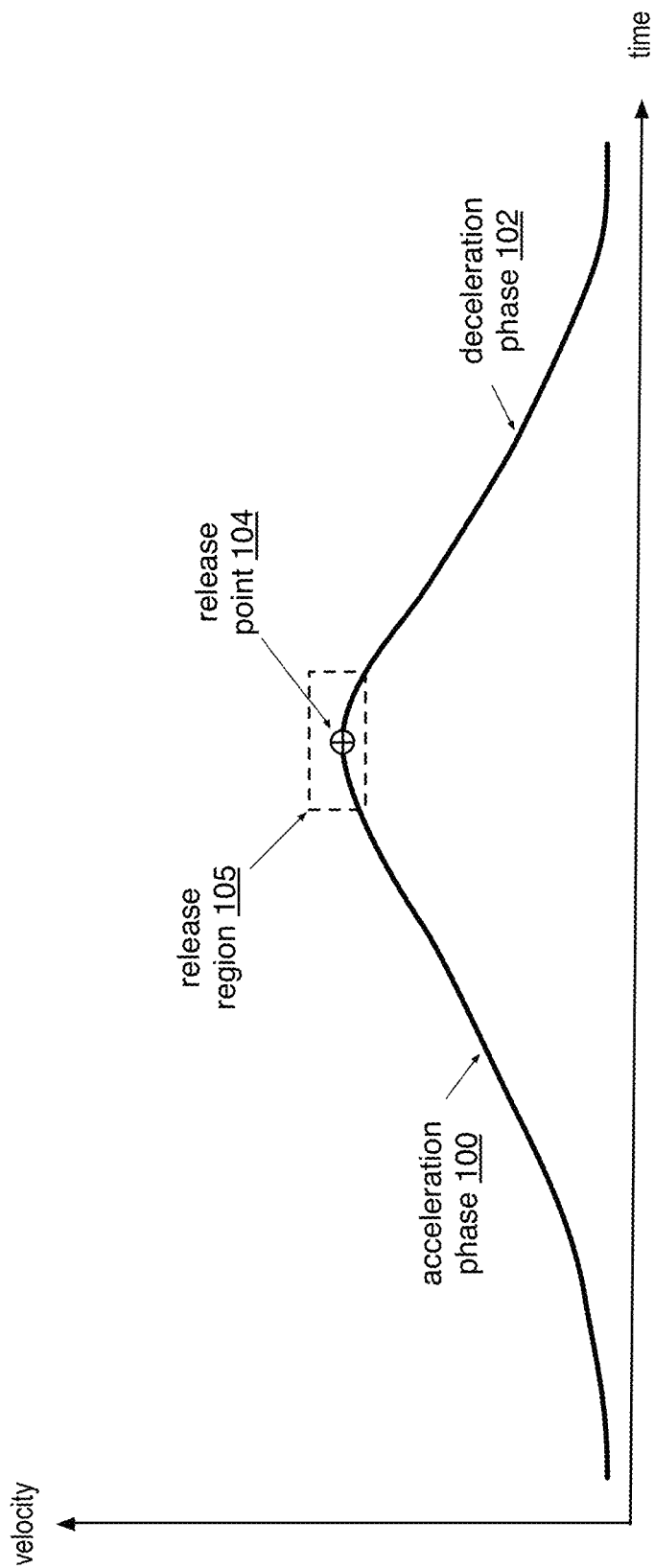
FIG. 27 is a diagram of an example determining a release region and a release point of a pitch in accordance with the present invention.

From this data and the steps performed to calculate it, the computing device determines the release point and/or release region. For example, the computing device may plot the velocity of a pitch over the duration of the pitch as shown in FIG. 27. Based on the assumption that the release point will occur when the velocity is at a maximum value, the release point 104 and/or the release region 105 can be determined. Note that, depending on the sampling rate, several sampling intervals may have substantially similar maximum velocities. In this instance, the several sampling intervals correspond to the release region 105. The middle of the release region 105 may be deemed to be the release point 104. With release point 104 determined, the sampling intervals preceding the release point 104 corresponds to the acceleration phase 100 and the sampling intervals subsequent to the release point 104 corresponds to the deceleration phase.

Figure 28:
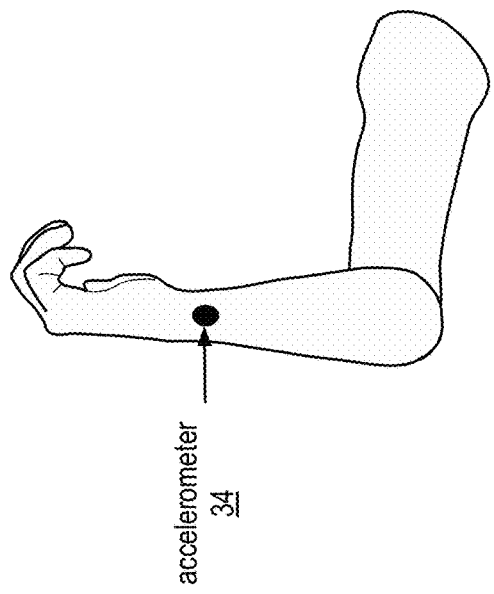
Figure 29:
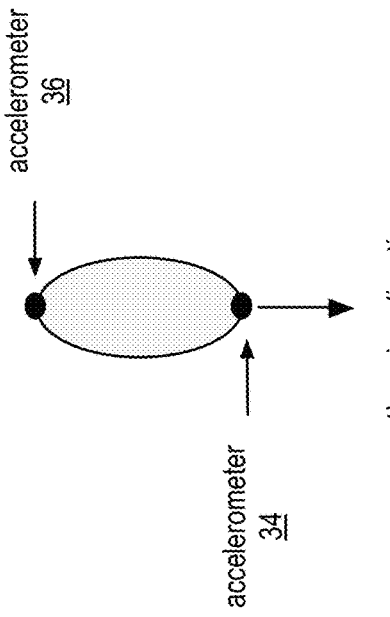

Knowing the release point, the computing device can then determine the arm orientation at the release point based on the location coordinates of the accelerometers at the release point. For example, FIGS. 28 and 29 illustrate front and top views of an arm orientation where a line between the radius distal area to ulnar distal area of the wrist is substantially parallel to home plate. This arm orientation corresponds to a fastball or a change up and typically places the less stress on the arm (e.g., the shoulder and the elbow).

Figure 30:
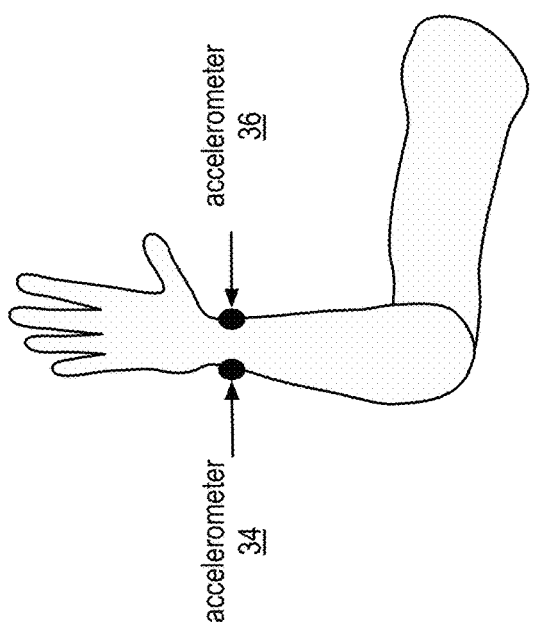
Figure 31:
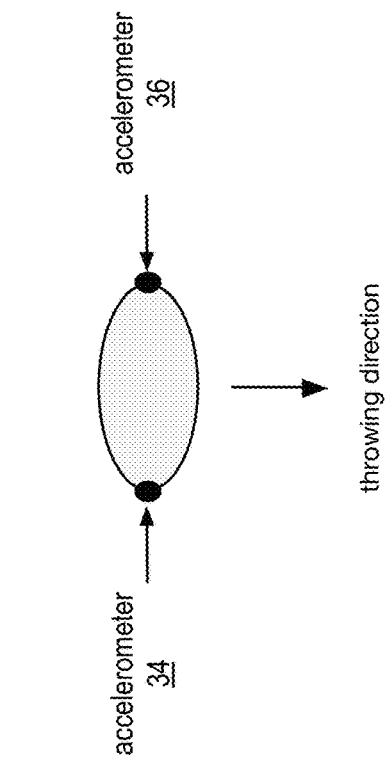

As another example, FIGS. 30 and 31 illustrate front and top views of an arm orientation where a line between the radius distal area to ulnar distal area of the wrist is not parallel to home plate. In particular, the ulnar distal area of the wrist is pointing towards home plate. This arm orientation corresponds to a curveball or a slider and typically places the more stress on the arm than the arm orientation of FIGS. 28 and 29. The amount of stress may be scaled based on the angle of rotation of the wrist. In the example of FIGS. 30 and 31, the wrist is at an angle of approximately 90 degrees. The angle of the wrist, however, may vary from just over 0 degrees to 90 degrees.

As yet another example, FIGS. 32 and 33 illustrate front and top views of an arm orientation where a line between the radius distal area to ulnar distal area of the wrist is not parallel to home plate. In particular, the radius distal area of the wrist is pointing towards home plate. This arm orientation corresponds to a screwball and typically places the more stress on the arm than the arm orientation of FIGS. 28 and 29. The amount of stress may be scaled based on the angle of rotation of the wrist. In the example of FIGS. 32 and 33, the wrist is at an angle of approximately 45 degrees. The angle of the wrist, however, may vary from just over 0 degrees to 90 degrees.

It is noted that terminologies as may be used herein such as bit stream, stream, signal sequence, etc. (or their equivalents) have been used interchangeably to describe digital information whose content corresponds to any of a number of desired types (e.g., data, video, speech, audio, etc. any of which may generally be referred to as 'data').

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "configured to", "operably coupled to", "coupled to", and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "configured to", "operable to", "coupled to", or "operably coupled to" indicates that an item includes one or more of power connections, input(s), output(s), etc., to perform, when activated, one or more its corresponding functions and may further include inferred coupling to one or more other items. As may still further be used herein, the term "associated with", includes direct and/or indirect coupling of separate items and/or one item being embedded within another item.

As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1. As may be used herein, the term "compares unfavorably", indicates that a comparison between two or more items, signals, etc., fails to provide the desired relationship.

As may also be used herein, the terms "processing module", "processing circuit", "processor", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, and/or processing unit may be, or further include, memory and/or an integrated memory element, which may be a single memory device, a plurality of memory devices, and/or embedded circuitry of another processing module, module, processing circuit, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, and/or processing unit executes, hard coded and/or operational instructions corresponding to at least some of the steps and/or functions illustrated in one or more of the Figures. Such a memory device or memory element can be included in an article of manufacture.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

In addition, a flow diagram may include a "start" and/or "continue" indication. The "start" and "continue" indications reflect that the steps presented can optionally be incorporated in or otherwise used in conjunction with other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

While the transistors in the above described figure(s) is/are shown as field effect transistors (FETs), as one of ordinary skill in the art will appreciate, the transistors may be implemented using any type of transistor structure including, but not limited to, bipolar, metal oxide semiconductor field effect transistors (MOSFET), N-well transistors, P-well transistors, enhancement mode, depletion mode, and zero voltage threshold (VT) transistors.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments. A module implements one or more functions via a device such as a processor or other processing device or other hardware that may include or operate in association with a memory that stores operational instructions. A module may operate independently and/or in conjunction with software and/or firmware. As also used herein, a module may contain one or more sub-modules, each of which may be one or more modules.

While particular combinations of various functions and features of the one or more embodiments have been expressly described herein, other combinations of these features and functions are likewise possible. The present disclosure is not limited by the particular examples disclosed herein and expressly incorporates these other combinations.

What is claimed is:

1. A method for execution by a computing device, the method comprises:
   wirelessly collecting via a wireless communication interface from at least two accelerometers, for a pitch, per pitch data that includes a plurality of first arm orientation data points and a plurality of second arm orientation data points;
   analyzing the per pitch data to determine a release point arm orientation and an effort level, wherein the release point arm orientation corresponds to one of a fastball, a curve ball, a slider, a screwball, or a knuckle ball;
   calculating a per pitch stress level based on the release point arm orientation, type of pitch, and the effort level, wherein the slider has a higher weighting factor than the fastball creating, for the same effort level, a higher per pitch stress level;
   calculating, for a set of pitches, a fatigue level based on the per pitch stress level of each pitch of the set of pitches; and
   outputting the fatigue level via a user interface.

2. The method of claim 1 further comprises:
   selecting the set of pitches from a plurality of pitches by:
      for each pitch of the plurality of pitches, determining whether the per pitch data indicates a warm-up pitch; and
      when, for one of the plurality of pitches, the per pitch data does not indicate a warm-up pitch, including the one of the plurality of pitches in the set of pitches.

3. The method of claim 1, wherein the analyzing the per pitch data to determine the release point arm orientation comprises:
   processing the plurality of first and second arm orientation data points to determine an acceleration phase of the pitch;
   processing the plurality of first and second arm orientation data points to determine a deceleration phase of the pitch;
   establishing a release region of the pitch based on the acceleration phase of the pitch and the deceleration phase of the pitch; and
   using data points of the plurality of first and second arm orientation data points corresponding to the release region of the pitch to determine the release point arm orientation.

4. The method of claim 1, wherein the analyzing the per pitch data to determine the effort level comprises:

utilizing at least one of the plurality of first arm orientation data points and the plurality of second arm orientation data points to determine an arm speed for the pitch; and calculating the effort level based on the arm speed for the pitch and historical arm speed data of a pitcher throwing the pitch.

5. The method of claim 1, wherein the calculating the per pitch stress level comprises:

determining a first weighting factor based on the release point arm orientation;

determining a second weighting factor based on the effort level; and calculating the per pitch stress level based on the first and second weighting factors.

6. The method of claim 1 further comprises:

establishing a fatigue level threshold; and generating one or more alarm indicators as the fatigue level approaches and exceeds the fatigue level threshold.

7. The method of claim 1, wherein the calculating the fatigue level comprises:

establishing an initial fatigue level; and utilizing the initial fatigue level as an offset when calculating the fatigue level based on the per pitch stress level of each pitch of the set of pitches.

8. The method of claim 1 further comprises:

cumulating, to produce cumulative pitching data, at least one of:

the fatigue level for a plurality of sets of pitches;

the release point arm orientation for the plurality of sets of pitches;

the effort level for the plurality of sets of pitches; and the per pitch stress level for the plurality of sets of pitches; and calculating historical pitching data for a pitcher based on the cumulative pitching data.

9. The method of claim 8 further comprises at least one of:

determining a recovery protocol based on the historical pitching data; and determining a training protocol based on the historical pitching data.

10. The method of claim 1, wherein the collecting the per pitch data comprises:

receiving the plurality of first arm orientation data points from a first sensor on a radius distal area of a pitcher's wrist; and receiving the plurality of second arm orientation data points from a second sensor on an ulnar distal area of the pitcher's wrist.

11. A non-transitory computer readable storage device comprises:

a first memory section that stores operational instructions that, when executed by a computing device, causes the computing device to:

wirelessly collect, via a wireless communication interface from at least two accelerometers, for a pitch, per pitch data that includes a plurality of first arm orientation data points and a plurality of second arm orientation data points;

a second memory section that stores operational instructions that, when executed by the computing device, causes the computing device to:

analyze the per pitch data to determine a release point arm orientation and an effort level, wherein the release point arm orientation corresponds to one of a fastball, a curve ball, a slider, a screwball, or a knuckle ball; and calculate a per pitch stress level based on the release point arm orientation, type of pitch, and the effort level, wherein the slider has a higher weighting factor than the fastball creating, for the same effort level, a higher per pitch stress level; and a third memory section that stores operational instructions that, when executed by the computing device, causes the computing device to:

calculate, for a set of pitches, a fatigue level based on the per pitch stress level of each pitch of the set of pitches; and output the fatigue level via a user interface.

12. The non-transitory computer readable storage device of claim 11, wherein the third memory section further stores operational instructions that, when executed by the computing device, causes the computing device to:

select the set of pitches from a plurality of pitches by:

for each pitch of the plurality of pitches, determining whether the per pitch data indicates a warm-up pitch; and when, for one of the plurality of pitches, the per pitch data does not indicate a warm-up pitch, include the one of the plurality of pitches in the set of pitches.

13. The non-transitory computer readable storage device of claim 11, wherein the second memory section further stores operational instructions that, when executed by the computing device, causes the computing device to analyze the per pitch data to determine the release point arm orientation by:

processing the plurality of first and second arm orientation data points to determine an acceleration phase of the pitch;

processing the plurality of first and second arm orientation data points to determine a deceleration phase of the pitch;

establishing a release region of the pitch based on the acceleration phase of the pitch and the deceleration phase of the pitch; and using data points of the plurality of first and second arm orientation data points corresponding to the release region of the pitch to determine the release point arm orientation.

14. The non-transitory computer readable storage device of claim 11, wherein the second memory section further stores operational instructions that, when executed by the computing device, causes the computing device to analyze the per pitch data to determine the effort level by:

utilizing at least one of the plurality of first arm orientation data points and the plurality of second arm orientation data points to determine an arm speed for the pitch; and calculating the effort level based on the arm speed for the pitch and historical arm speed data of a pitcher throwing the pitch.

15. The non-transitory computer readable storage device of claim 11, wherein the second memory section further stores operational instructions that, when executed by the computing device, causes the computing device to calculate the per pitch stress level by:

determining a first weighting factor based on the release point arm orientation;

determining a second weighting factor based on the effort level; and calculating the per pitch stress level based on the first and second weighting factors.

16. The non-transitory computer readable storage device of claim 11, wherein the third memory section further stores operational instructions that, when executed by the computing device, causes the computing device to:
establish a fatigue level threshold; and
generate one or more alarm indicators as the fatigue level approaches and exceeds the fatigue level threshold.

17. The non-transitory computer readable storage device of claim 11, wherein the third memory section further stores operational instructions that, when executed by the computing device, causes the computing device to calculate the fatigue level by:
establishing an initial fatigue level; and
utilizing the initial fatigue level as an offset when calculating the fatigue level based on the per pitch stress level of each pitch of the set of pitches.

18. The non-transitory computer readable storage device of claim 11 further comprises:
a fourth memory section that stores operational instructions that, when executed by the computing device, causes the computing device to:
cumulate, to produce cumulative pitching data, at least one of:
the fatigue level for a plurality of sets of pitches;
the release point arm orientation for the plurality of sets of pitches;
the effort level for the plurality of sets of pitches; and
the per pitch stress level for the plurality of sets of pitches; and
calculate historical pitching data for a pitcher based on the cumulative pitching data.

19. The non-transitory computer readable storage device of claim 18, wherein the fourth memory section further stores operational instructions that, when executed by the computing device, causes the computing device to perform at least one of:
determining a recovery protocol based on the historical pitching data; and
determining a training protocol based on the historical pitching data.

20. The non-transitory computer readable storage device of claim 11, wherein the first memory section further stores operational instructions that, when executed by the computing device, causes the computing device to collect the per pitch data by:
receiving the plurality of first arm orientation data points from a first sensor on a radius distal area of a pitcher's wrist; and
receiving the plurality of second arm orientation data points from a second sensor on an ulnar distal area of the pitcher's wrist.

* * * * *